(12) United States Patent
Luo et al.

(10) Patent No.: US 9,441,241 B2
(45) Date of Patent: Sep. 13, 2016

(54) METHODS AND COMPOSITIONS FOR TRANSGENIC PLANTS WITH ENHANCED RESISTANCE TO BIOTIC AND ABIOTIC STRESS

(71) Applicant: Clemson University, Anderson, SC (US)

(72) Inventors: Hong Luo, Clemson, SC (US); Halina Knap, Clemson, SC (US); Zhigang Li, Clemson, SC (US); April Warner, Seneca, SC (US); Qian Hu, Clemson, SC (US)

(73) Assignee: Clemson University, Anderson, SC (US)

( * ) Notice: Subject to any disclaimer, the term of this patent is extended or adjusted under 35 U.S.C. 154(b) by 74 days.

(21) Appl. No.: 14/173,639

(22) Filed: Feb. 5, 2014

(65) Prior Publication Data

US 2014/0237684 A1 Aug. 21, 2014

Related U.S. Application Data

(60) Provisional application No. 61/761,148, filed on Feb. 5, 2013.

(51) Int. Cl.
*C07K 14/415* (2006.01)
*C12N 15/29* (2006.01)
*C12N 15/82* (2006.01)
*C07K 14/81* (2006.01)

(52) U.S. Cl.
CPC ....... *C12N 15/8286* (2013.01); *C07K 14/8139* (2013.01); *C12N 15/8271* (2013.01); *C12N 15/8273* (2013.01); *C12N 15/8279* (2013.01); *C12N 15/8285* (2013.01)

(58) Field of Classification Search
None
See application file for complete search history.

(56) References Cited

U.S. PATENT DOCUMENTS

2003/0236208 A1* 12/2003 Kmiec et al. .................. 514/44
2004/0031072 A1* 2/2004 La Rosa et al. .............. 800/278
2004/0216190 A1* 10/2004 Kovalic ........................ 800/289

OTHER PUBLICATIONS

Schmutz et al. (Nature 463:178-183(2010)).*
Schluter et al. (Journal of Experimental Botany, vol. 61, No. 15, pp. 4169-4183, 2010).*
Alvarez-Alfageme et al. "Effects of potato plants expressing a barley cystatin on the predatory bug *Podisus maculiventris* via herbivorous prey feeding on the plant" *Transgenic Res* 16:1-13 (2007).
Behnke et al. "Developing novel anthelmintics from plant cysteine proteinases" *Parasites & Vectors* 1(29):1-18 (2008).
Benchabane et al. "Plant cystatins" *Biochimie* 92:1657-1666 (2010).
Botella et al. "Differential Expression of Soybean Cysteine Proteinase Inhibitor Genes during Development and in Response to Wounding and Methyl Jasmonate" *Plant Physiol.* 112:1201-1210 (1996).
Delheimer "Comparison of the Effects of the SCN Resistance Gene rhg1 from PI 88788, PI 437654, and Two SCN Resistance QTL from Glycine soja PI 468916" *ASA-CSSA-SSSA International Annual Meetings*, New Orleans, LA Nov. 4-8, 2007 (Abstract).
Gheysen et al. "RNAi from plants to nematodes" *Trends in Biotechnology* 25(3):89-92 (2007).
Grudkowska et al. "Multifunctional role of plant cysteine proteinases" *Acta Biochimica Polonica* 51(3):609-624 (2004).
Li et al. "GmCPI1, a soybean cysteine protease inhibitor is involved in plant response to biotic stress" Poster presented at Clemson University Feb. 5, 2014 (1 page).
Martinez et al. "C1A cysteine-proteases and their inhibitors in plants" *Physiologia Plantarum* 145:85-94 (2012).
McKerrow et al. "Cysteine Protease Inhibitors as Chemotherapy for Parasitic Infections" *Bioorganic & Medicinal Chemistry* 7:639-644 (1999).
NCBI Reference Sequence XM_003524865.1 "Predicted: Glycine max cysteine proteinase inhibitor 10-like, transcript variant 1 (LOC100809340), mRNA" Nov. 8, 2011 (1 page).
NCBI Reference Sequence: XM_003524866.1 "Predicted: Glycine max cysteine proteinase inhibitor 10-like, transcript variant 2 (LOC100809340), mRNA" Nov. 8, 2011 (1 page).
NCBI Reference Sequence: XP_003524913.1 "Predicted: Cysteine proteinase inhibitor 10-like isoform 1 [Glycine max]" Nov. 8, 2011 (1 page).
NCBI Reference Sequence XP_003524914.1 "Predicted: cysteine proteinase inhibitor 10-like isoform 2 [Glycine max]" Nov. 8, 2011 (1 page).
Rashed et al. "Protease Inhibitor Expression in Soybean Roots Exhibiting Susceptible and Resistant Interactions with Soybean Cyst Nematode" *Journal of Nematology* 40(2):138-146 (2008).
Sablok et al. "Artificial microRNAs (amiRNAs) engineering—On how microRNA-based silencing methods have affected current plant silencing research" *Biochemical and Biophysical Research Communications* 406:315-319 (2011).
Slide set for presentation to United Soybean Board, Feb. 20-21, 2011 (13 pages).
Slide set for presentation to United Soybean Board, Mar. 5, 2012 (15 pages).
Solomon et al. "The Involvement of Cysteine Proteases and Protease Inhibitor Genes in the Regulation of Programmed Cell Death in Plants" *The Plant Cell* 11:431-443 (1999).
Stepek et al. "Natural plant cysteine proteinases as anthelmintics?" *Trends in Parasitology* 20(7):322-327 (2004).
Tomkins et al. "A bacterial artificial chromosome library for soybean PI 437654 and identification of clones associated with cyst nematode resistance" *Plant Molecular Biology* 41:25-32 (1999).
Yan et al. "Effective Small RNA Destruction by Expression of a Short Tandem Target Mimic in Arabidopsis" *The Plant Cell* 24:415-427 (2012).

\* cited by examiner

*Primary Examiner* — Anne Kubelik
*Assistant Examiner* — Charles Logsdon
(74) *Attorney, Agent, or Firm* — Myers Bigel & Sibley, P.A.

(57) ABSTRACT

The present invention provides methods and compositions for producing transgenic plants having increased resistance to biotic and/or abiotic stress and comprising an exogenous nucleotide sequence encoding a cysteine protease inhibitor.

23 Claims, 13 Drawing Sheets

Figure 1

```
Query seq.
Superfamilies
                              CY Superfamily

>Glyma05g28250 peptide_5|130_aa
MAALIRSPAV IIAIIITISAC IACTASYGGL VGGRSKIPDV RANKKVQDLG
RFSVEEHNRM LRQAQKEEEQ VTFVEVVEAQ QQVVSGIKYY MKISATQGGD
GGDSRIFESV VVVKPWLRSK QLLNFAPSTQ K=Lysine >PI_130_aa
MAALIRSPAV IIAIIITISAC IACTASYGGL VGGRSKIPDV RANKEVQDLG
RFSVEEHNRM LRQAQKEEEQ VTFVEVVEAQ QQVVSGIKYY MKISATQGGD
GGDSRIFESV VVVKPWLRSK QLLNFAPSTQ E=Glutamic acid Protein: Identities = 129/130 (99%), Positives = 130/130
(100%), Gaps = 0/130 (0%)

>lcl|51033 PI 130_aa
Length=130

Score =  265 bits (677),  Expect = 2e-76, Method: Compositional matrix adjust.
Identities = 129/130 (99%), Positives = 130/130 (100%), Gaps = 0/130 (0%)

Query  1    MAALIRSPAVIIAIIITISACIACTASYGGLVGGRSKIPDVRANKKVQDLGRFSVEEHNRM  60
            MAALIRSPAVIIAIIITISACIACTASYGGLVGGRSKIPDV+ANK+VQDLGRFSVEEHNRM
Sbjct  1    MAALIRSPAVIIAIIITISACIACTASYGGLVGGRSKIPDVRANKEVQDLGRFSVEEHNRM  60

Query  61   LRQAQKEEEQVTFVEVVEAQQQVVSGIKYYMKISATQGGDGGDSRIFESVVVVKPWLRSK  120
            LRQAQKEEEQVTFVEVVEAQQQVVSGIKYYMKISATQGGDGGDSRIFESVVVVKPWLRSK
Sbjct  61   LRQAQKEEEQVTFVEVVEAQQQVVSGIKYYMKISATQGGDGGDSRIFESVVVVKPWLRSK  120

Query  121  QLLNFAPSTQ  130
            QLLNFAPSTQ
Sbjct  121  QLLNFAPSTQ  130
```

SEQUENCE LISTING

```
<160> NUMBER OF SEQ ID NOS: 8

<210> SEQ ID NO 1
<211> LENGTH: 130
<212> TYPE: PRT
<213> ORGANISM: Glycine max
```

<400> SEQUENCE: 1

Met Ala Ala Leu Ile Arg Ser Pro Ala Val Ile Leu Ala Ile Leu Thr
1               5                   10                  15

Ile Ser Ala Cys Ile Ala Cys Thr Ala Ser Tyr Gly Gly Leu Val Gly
            20                  25                  30

Gly Arg Ser Lys Ile Pro Asp Val Lys Ala Asn Lys Lys Val Gln Asp
        35                  40                  45

Leu Gly Arg Phe Ser Val Glu Glu His Asn Arg Met Leu Arg Gln Ala
    50                  55                  60

Gln Lys Glu Glu Glu Gln Val Thr Phe Val Val Val Glu Ala Gln
65                  70                  75                  80

Gln Gln Val Val Ser Gly Ile Lys Tyr Tyr Met Lys Ile Ser Ala Thr
                85                  90                  95

Gln Gly Gly Asp Gly Gly Asp Ser Arg Ile Phe Glu Ser Val Val Val
            100                 105                 110

Val Lys Pro Trp Leu Arg Ser Lys Gln Leu Leu Asn Phe Ala Pro Ser
        115                 120                 125

Thr Gln
    130

<210> SEQ ID NO 2
<211> LENGTH: 641
<212> TYPE: DNA
<213> ORGANISM: Glycine max

<400> SEQUENCE: 2
atcgttctaa attaattcta acaggttcgg cataattgag cgatcgatgg cggcgttgat      60
aaggtcaccg gcggtgatac tggcgatcct gacgatctcg gcgtgcatcg cgtgtacggc     120
gtcgtacggg ggattggtcg ggggaaggtc gaagatccct gacgtgaagg cgaacaagaa     180
ggtgcaggat ctagggcggt tctcggtgga ggagcataac cggatgctga ggcaggcgca     240
gaaggaggag gagcaagtca cgttcgtgga agtggtggag gcgcaacaac aagtggtgtc     300
tgggatcaag tactacatga agatatcggc cacgcagggt ggcgacggtg agattccag     360 aatattcgaa tccgttgtgg tggtgaagcc gtggcttcgt tccaagcagc ttctcaattt     420
cgctccttcc acgcagtgaa atacgatcaa tttcggttcc gtttcaatta cttttttaac     480
tcataataac atgcttaatt ggtttagtat gctttaatcc ttctaataaa aaatatgaaa     540
gagagaaata aatgtttaca atttctgttt cagacatgaa tcaactggtt aacaggttaa     600
caataatgtc aaagatatat ttacattgtt ttgagcatgg a                         641

<210> SEQ ID NO 3
<211> LENGTH: 130
<212> TYPE: PRT
<213> ORGANISM: Glycine max

<400> SEQUENCE: 3

Met Ala Ala Leu Ile Arg Ser Pro Ala Val Ile Leu Ala Ile Leu Thr
1               5                   10                  15

Ile Ser Ala Cys Ile Ala Cys Thr Ala Ser Tyr Gly Gly Leu Val Gly
            20                  25                  30

Gly Arg Ser Lys Ile Pro Asp Val Lys Ala Asn Lys Glu Val Gln Asp
        35                  40                  45

Leu Gly Arg Phe Ser Val Glu Glu His Asn Arg Met Leu Arg Gln Ala
    50                  55                  60

Gln Lys Glu Glu Gln Val Thr Phe Val Glu Val Glu Ala Gln
65                  70                  75                  80

Gln Gln Val Val Ser Gly Ile Lys Tyr Tyr Met Lys Ile Ser Ala Thr
                85                  90                  95

Gln Gly Gly Asp Gly Gly Asp Ser Arg Ile Phe Glu Ser Val Val Val
            100                 105                 110

Val Lys Pro Trp Leu Arg Ser Lys Gln Leu Leu Asn Phe Ala Pro Ser
        115                 120                 125

Thr Gln
    130

<210> SEQ ID NO 4
<211> LENGTH: 607
<212> TYPE: DNA
<213> ORGANISM: Glycine max

<400> SEQUENCE: 4
atcgttctaa attaattcta acaggttcgg cataattgag cgatcgatgg cggcgttgat       60
aaggtcaccg gcggtgatac tggcgatcct gacgatctcg gcgtgcatcg cgtgtacggc      120
gtcgtacggg ggattggtcg ggggaaggtc gaagatccct gacgtgaagg cgaacaagaa      180
ggtgcaggat ctagggcggt tctcggtgga ggagcataac cggatgctga ggcaggcgca      240
gaaggaggag gagcaagtca cgttcgtgga agtggtggag cgcaacaac aagtggtgtc       300 tgggatcaag tactacatga agatatcggc cacgcagggt ggcgacggtg agattccag       360 aatattcgaa tccgttgtgg tggtgaagcc gtggcttcgt tccaagcagc ttctcaattt      420
cgctccttcc acgcagtgaa atacgatcaa tttcggttcc gtttcaatta cttttttaac      480
tcataataac atgcttaatt ggtttagtat gctttaatcc ttctaataaa aaatatgaaa      540
gagagaaata aatgtttaca atttctgttt cagacatgaa tcaactggtt aacaggttga      600
attgtac                                                                607

<210> SEQ ID NO 5
<211> LENGTH: 393
<212> TYPE: DNA
<213> ORGANISM: Glycine max

<400> SEQUENCE: 5
atggcggcgt tgataaggtc accggcggtg atactggcga tcctgacgat ctcggcgtgc       60
atcgcgtgta cggcgtcgta cgggggattg gtcgggggaa ggtcgaagat ccctgacgtg      120
aaggcgaaca aggaggtgca ggatctaggg cggttctcgg tggaggagca taaccggatg      180
ctgaggcagg cgcagaagga ggaggagcaa gtcacgttcg tggaagtggt ggaggcgcaa      240
caacaagtgg tgtctgggat caagtactac atgaagatat cggccacgca gggtggcgac      300
ggtggagatt ccagaatatt cgaatccgtt gtggtggtga agccgtggct tcgttccaag      360
cagcttctca atttcgctcc ttccactcag tga                                    393

<210> SEQ ID NO 6
<211> LENGTH: 5890
<212> TYPE: DNA
<213> ORGANISM: Glycine max

<400> SEQUENCE: 6
actaattctt gaggaaagac aggaagaaat agataaaaag aaaaagaaaa aaggaagaag       60
aggaagaaat caactgcagt ataaagtcca gaacccaata cataataata taattttaaa      120

```
acaagataaa taataataaa ataattacag catgatggta gacgcgtggt ggccaacaac    180
ggttccatgg ccaaatcgaa ggctcgtgca gccatgggcc catcacgaga aacctggacc    240
ggaagagggc ggaacggagt ggagtgggtg ggaaaggaaa aagagggta aaaaagaag      300 aaagaagaga aattatatag ataaataaat aatttaagta agaataaatt ttgtatttcc    360
gtttcaaaat aaaaaatata tatataatta atcatttaa aataaatatt agaaggtaag     420
tcttttgtga gatttaaaaa aagattttag atctaaaaat gagatttgct attagattaa    480
aaaatttaaa aagtatgata cggataaatt tatcaaaaaa attattaaga tctcaaaaat    540
aaaatctatt atgagaggag ttcttggaag catacagtat cctccaaaaa aagaaaagaa    600
gggatgaaca gtttattagt ttcaagtttt ccatttgag tcaagtgtta atctacatag     660
aatttgagta aacaatttaa taacacgtag cctccgaaac ataataaatt tggccgttta    720
gaaaagcaat aaacaagttc tcgagggatt tctagcaacg atgccgttgt gctcaaattc    780
ttgtcgaatt ttttctatga tcgatcttcc accatgagat ttgactttcc tcacattttc    840
aagtttctgc aatgcattct ttcttcaacc tcataacccg ttccttcaaa actgcttttg    900
gaagtagtgg ctaccttatt ccgatgagct tcgaggactg ccttctcatc atttatagca    960
aaggcttgtt tgatggaata tagaatgctt gggaactctt tgcgcttaga gtatatcata   1020
tctttaagtt catatgtaca tctgtgaata atctgtctta cctttgaata tcgggcgata   1080
aggataaata ggagtcaaca acttgtttgc aatgaggctc tataatgacg ttttgcatat   1140
tcaattcatt ctacttttgg tcccagtaat tttaaaatca atcaatttga tcttataagt   1200
ttaaaaatag ataaatttaa tccttaggct tcgattgttg agaaactaaa aatagactaa   1260
atttatcttc ttttttttaa cataaagatc aaactgatcg gtttaaaatt acagcgacta   1320
aaattaaatt ttgttcaatc tttaaaaacc tattttagcc ttaaatcttg tgatccataa   1380
ctatatatta atacatttta ttgcatgatt tttacttctt ctttttatct ccacagata   1440 taaacattta ccaaatgtag tcatttatgt tcatacactt tcacataaac agttgtcttt   1500
gtgatacatt ctacataaaa cttgtgtacc aagaaagaag aaaatacatc tttgtaataa   1560
aagcaactga ggtagtttta attatggtag taattgcctt ttgtcattct tcctcagcag   1620
tcatccccat ggctcaggaa tatggggctc gtgtacccc cttggaattg ggctgagtat    1680
tcgttgaaca tagccacgtc tctatagcct ttttcagtca gaattaacaa tcgtcataat   1740
aaattaatca tgagtagtat taataattag gctagaatta ccagttacaa gtagcaaaaa   1800
ctacaaatat tactcctttt ttcacctggt ttatctcttt cgtattaaat ttcacctaat   1860
ttatttcttt cgtattaata tgaccttat tataaagcaa tcattcatca caagagtgag    1920
gcagaataca aatggcatac aaaattttac ttttatattt gatagtttat agctcaacca   1980
tttgatgaaa cacaaaagat acgagaagag acacgaaaaa taccaccaca aaaagcttga   2040
gcggagtcta tatatacacg aagaaagtca tctacttatt ctattataat aattattaat   2100
tatttattct atctcataat tattttaaa atttgtaccc tcctaatcgt cgatccacac    2160
ttagatgagt gccaattgac ctcattagga cagcaaaaat taacacttta atcttatctc   2220
aaagtcatat ttacggcacc atacgagata taatgtggaa ttgaacccaa aggaatgtag   2280
gttacaaata tacacttaga tgctctaact actggttctt tcaattctag ttctaggaac   2340
gatttatatt ggaataaaat taaacatgaa ataagtgtta tgcattacta atatttatct   2400
agctctcaac aacaaatcta atgcattaaa gtgtaactga accaaacacc atcttaaaaa   2460
```

```
caatagaatt aaactgaaaa aaaaaattat aaattaatcc gtgtatagtg gcgggacagt    2520
tatgcaaact gcatgtagta tacgtggaag cctctgagat tagtgctagc caatgtgtca    2580
gtttgtggta accacaccaa gccaactcga tcgtgactag acccgtttac ggcaacaacc    2640
ttaaacaaac aaaaatgaaa aagcaatctc gtttgcatcc aaaactcgcg tcccaatcgc    2700
gacacgcacg cggttttcgt ttccccacca ttcaccgtct ctcggttagt ttttcatgcg    2760
tatccaaaca cctctttccc cctttatata aacgacaccg tatacgcaac tccatcatcg    2820
ttctaaatta attctaacag gttcggcata attgagcgat cgatggcggc gttgataagg    2880
tcaccggcgg tgatactggc gatcctgacg atctcggcgt gcatcgcgtg tacggcgtcg    2940 tacggggat tggtcggggg aaggtcgaag atccctgacg tgaaggcgaa caaggaggtg    3000
caggatctag ggcggttctc ggtggaggag cataaccgga tgctgaggca ggcgcagaag    3060
gaggaggagc aagtcacgtt cgtggaagtg gtggaggcgc aacaacaagt ggtgtctggg    3120
atcaagtact acatgaagat atcggccacg cagggtggcg acggtggaga ttccagaata    3180
ttcgaatccg ttgtggtggt gaagccgtgg cttcgttcca agcagcttct caatttcgct    3240
ccttccactc agtgaaatac gatcaatttc ggttccgttt caactacttt tttaactcat    3300
aataacatgc ttaattggtt tagtatgctt taatccttct aataaaaaat atgaaagaga    3360
gaaataaatg tttacaattt ctgtttcaga catgaatcaa ctagtgaaca ggttaaattg    3420
tcaaatatct aaagatatat ttacattgtt ttgagcatga gtctctctat gttttttta    3480 atctactatg ggcatatttt atcttagagg agtgatactt tgtacagata tcatttctct    3540 aactttatt atcatttata aacgttaaac gatattatta tgaagtttgt ctcaatgaat    3600
taaaatgttt aggttattaa gactggataa tctaggcgtg tattcaatta cgacgtttat    3660
ttcgtggaca ttttttttg tctcgggaat ttatttattt tttcctcata atatagcatg    3720
acaatgttat ttttgggttc cttatatatg ctctaaaaaa attgtttggt taattattaa    3780
aattgactgt aaatgttttt tatattctca taaataaaac acgtgtgctt gattgagtta    3840 tttttttgt tgagagtttg attgagttat taatttctaa cttgcataa gtgataagta    3900 agttttctat ctaataacat acacataaca cctttcagta tgtaactgag tatcttcac    3960 gaatatatat atatatatat atatatagag agagagagag agagagagag agagagagag    4020
agagagagag agcaattc caatatgcct attttgcgtg acaatgttat ttatttttt    4080 tttgtctcgg gaatttattt atttttcct cataatatag catgacaatg ttatttttgg    4140
gttccttata tatgctctaa aaaaattgtt tggttaatta ttaaaattga ctgtaaatgt    4200
tttttatatt ctcataaata aaacacgtgt gcttgattga gttattttt ttgttgagag    4260 tttgattgag ttattaattt ctaactttgc ataagtgata agtaagtttt ctatctaata    4320
acatacacat aacaccttc agtatgtaac tgagtatctt tcacgaatat atatatatat    4380
atatatatat agagagagag agagagagag agagagagag agagagagag agagagagag    4440
agagagagag agagagagag agagagagag agagagagag agagagagag agagagcaat    4500
tccaatatgc ctattttgcg tgaatgaaat tggcacatag ggatgaaaat tgtggcaaag    4560 aaaaaaact atattatgta acatgaagga ggagcattga gagggtagta cggagaatat    4620
gtttggattt ttattcataa agagatttct gtcacgagaa taaatttca tagttttacg    4680 ttcaataata aacagaataa ctttatagt tataataatg gtagtattag gaattatttt    4740
agctatttct caacaaaata ttaagaaaat tttggtctat tacacgatgt ctcgattgaa    4800
ttatatgatc taggtatggg atattatgga gtccgagatt aaatattaat cctacgtaaa    4860
```

```
ttataactta catagaaata aaatatgttt aaaattaatt attttattac ttcataataa    4920
atatgggata aaaatttcta cctgtattcg tgggattaca aaaattaatt gagtaagacc    4980
gcttctccat ctgtcattat tgaattgttg agaagatata tacaaaatat tttggtgaaa    5040
aattacaggg aataaaaaaa ttgtataagg tataatactt ttaatgaaag atataagaag    5100
atattttatt gttattattt agtcattgag taaattttttt tttaagaaat atataaggac    5160
gtcttacaat agtgcaaata gcatttcaca tttgagtata aaaagtattt cgtcaacttt    5220
ttctcttctt taaatcaaat cgtcctctag ccatactttt tttatctaaa aaagtttaag    5280
ataaatatga agagatctac accaacttat taattatatt tttatttat ttaaaaagtt    5340 aaaaaaaaaa ctacagagag acttgcctct tattttcttc aatatagaa ataagaataa    5400 taaacactca aagaaaaaa atattagaaa aaaaataaga attatttcag gtaaatataa    5460
ttttgatgtc tgaaaatgtg aaatgataac aaattggtcg ctagaaaaac tcaaatttag    5520
tttttcaaat ataaaaaat ataattgatt agtcatatac acaatttaat gacaaattaa    5580
tacataaatt ttatagttta atgttaaatt aattttttaaa aatataattt atttttaaat    5640 tatttttttaa atattataac ttaattacaa aataatttca taaatttaac aataataata    5700
tattacagtt tttacacatt cattgtattt aaatttttta tctttaaaca accaataatt    5760
tatttatttt tttctaagaa aaacgacaag ctcaatatag aaactagaaa gtaaatttat    5820
tttatcaggt acacacaaga accgtacacg cgctgacatt caaatccctc ccatttccca    5880
actcccaact                                                          5890

<210> SEQ ID NO 7
<211> LENGTH: 686
<212> TYPE: DNA
<213> ORGANISM: Glycine max

<400> SEQUENCE: 7
atcgttctaa attaattcta acaggttcgg cataattgag cgatcgatgg cggcgttgat     60
aaggtcaccg gcggtgatac tggcgatcct gacgatctcg gcgtgcatcg cgtgtacggc    120
gtcgtacggg ggattggtcg ggggaaggtc gaagatccct gacgtgaagg cgaacaagaa    180
ggtgcaggat ctagggcggt tctcggtgga ggagcataac cggatgctga ggcaggcgca    240
gaaggaggag gagcaagtca cgttcgtgga agtggtggag gcgcaacaac aagtggtgtc    300
tgggatcaag tactacatga agatatcggc cacgcagggt ggcgacggtg gagattccag    360
aatattcgaa tccgttgtgg tggtgaagcc gtggcttcgt tccaagcagc ttctcaattt    420
cgctccttcc acgcagtgaa atacgatcaa tttcggttcc gtttcaatta cttttttaac    480
tcataataac atgcttaatt ggtttagtat gctttaatcc ttctaataaa aaatatgaaa    540
gagagaaata aatgtttaca atttctgttt cagacatgaa tcaactggtt aacaggttaa    600
caataatgtc aaagatatat ttacattgtt ttgagcatgg agtctctcta tgttttttt    660 tttaatctac tatgggcata tttttat                                       686

<210> SEQ ID NO 8
<211> LENGTH: 5652
<212> TYPE: DNA
<213> ORGANISM: Glycine max

<400> SEQUENCE: 8
ttgtatctct tcctaactaa ttcttgagga aagacaggaa gaaaagaaa aaggaagaa      60
```

-continued

| | | | | | |
|---|---|---|---|---|---|
| gaggaagaaa | tcaactgcag | tataaagtcc | agaaccgaat | acataataat | ataattttaa | 120 |
| aacaagataa | ataataataa | aataattaca | gcatgatggt | agacgcgtgg | tggccaacaa | 180 |
| cggttccatg | gccaaatcga | aggctcgtgc | agccatgggc | ccatcacgag | aaacctggac | 240 |
| cggaagaggg | cggaacggag | tggagtgggt | gggaaaggaa | aaagaggggt | aaagaaagaa | 300 |
| gaaagaagag | aaattatata | gataaataaa | taatttaagt | aagaatagat | tttgtatttc | 360 |
| cgtttcaaaa | taaaaatat | atatataatt | aatcatttta | aaataaatta | taaataaata | 420 |
| ttagaaggta | agtctttttgt | gagatttaaa | aaagatttt | agatctaaaa | atgagatttg | 480 |
| ctattagatt | aaaaaattta | aaagtatga | tacggataaa | tttatcaaaa | aatttattaa | 540 |
| gatctcaaaa | ataaaatctg | ttatgagagg | agttcttgga | agcatacagt | atcctccaaa | 600 |
| aaaagaaaag | aagggatgaa | cagtatatta | gtttcaagtt | ttccatttttg | agtcaagtgt | 660 |
| taatctacat | agaatttgag | taaacaattt | aataacacat | agcctccgaa | acataataaa | 720 |
| tttggccgtt | tagaaaagca | ataaacaagt | tctcgaggga | tttctagcaa | cgatgccgtt | 780 |
| gtgctcaaat | tcttgtcgaa | ttttttctat | gatcgatctt | ccaccatgag | atttgacttt | 840 |
| cctcacattt | tcaagtttct | gcaatgcatt | cttttcttcaa | cctcataacc | cgttccttca | 900 |
| aaactgcttt | tggaagtagt | ggctacctta | ttccgatgag | cttcgaggac | tgccttctca | 960 |
| tcatttatag | caaaggcttg | tttgatggaa | tatagaatgc | ttgggaactc | tttgcgctta | 1020 |
| gagtatatca | tatctttaag | ttcatatgta | catctgtgaa | taatctgtct | tacctttgaa | 1080 |
| tatcgggcga | taaggataaa | taggagtcaa | caacttgttt | gcaatgaggc | tctataatga | 1140 |
| cgttttgcat | attcaattca | ttctactttt | ggtcccagta | attttaaaat | caatcaattt | 1200 |
| gatcttataa | gtttaaaaat | agataaattt | aatccttagg | cttcgattgt | tgagaaacta | 1260 |
| aaaatagact | aaatttatct | tcttttttt | taacataaag | atcaaactga | tcggtttaaa | 1320 |
| attacagcga | ctaaaattaa | attttgttca | atctttgaaa | acctattta | gccttaattc | 1380 |
| ttgtgatcca | taactatata | ttaatacatt | ttattgcatg | attttacttt | cttcttttta | 1440 |
| tctccacgag | atataaacat | ttaccaaatg | tagtcattta | tgttcataca | ctttcacata | 1500 |
| aacagttgtc | tttgtgatac | attctacata | aaacttgtgt | accaagaaag | aagaaaatac | 1560 |
| atctttgtaa | taaaagcaac | tgaggtagtt | ttaattatgg | tagtaattgc | cttttgtcat | 1620 |
| tcttcctcag | cagtcatccc | catggctcag | gaatatgggg | ctcgtgtacc | ccccttggaa | 1680 |
| ttgggctgag | tattcgttga | acatagccac | gtctctatag | ccttttttcag | tcagaattaa | 1740 |
| caatcgtcat | aataaattaa | tcatgagtag | tattaataat | taggctagaa | ttaccagtta | 1800 |
| caagtagcaa | aaactacaaa | tattactcct | tttttcacct | ggtttatctc | tttcgtatta | 1860 |
| aatttcacct | aatttatttc | tttcgtatta | atatgacctt | tattataaag | caatcattca | 1920 |
| tcacaagagt | gaggcagaat | acaaatggca | tacaaaattt | tacttttata | tttgatagtt | 1980 |
| tatagctcaa | ccatttgatg | aaacacaaaa | gatacgagaa | gagacacgaa | aaataccacc | 2040 |
| acaaaaagct | tgagcggagt | ctatatatac | acgaagaaag | tcatctactt | attctattat | 2100 |
| aataattatt | aattatttat | tctatctcat | aattattttt | aaaatttgta | ccctcctaat | 2160 |
| cgtcgatcca | cacttagatg | agtgccaatt | gacctcatta | ggacagcaaa | aattaacact | 2220 |
| ttaatcttat | ctcaaagtca | tatttacggc | accatacgag | ataatgtg | gaattgaacc | 2280 |
| caaaggaatg | taggttacaa | atatacactt | agatgctcta | actactggtt | ctttcaattc | 2340 |
| tagttccagg | aacgatttat | attggaataa | aattaaacat | gaataagtg | ttatgcatta | 2400 |
| ctaatatttta | tctagctctc | aacaacaaat | ctaatgcatt | aaagtgtaac | tgaagcaaac | 2460 |

```
accatcttaa aaacaataga attaaactga aaaaaaaaat tataaattaa tccgtgtata    2520
gtggcgggac agttatgcaa actgcatgta gtatacgtgg aagcctctga gattagtgct    2580
agccaatgtg tcagtttgtg gtaaccacac caagccaact cgatcgtgac tagacccgtt    2640
tacggcaaca accttaaaca aacaaaaatg aaaaagcaat ctcgtttgca tccaaaactc    2700
gcgtcccaat cgcgacacgc acgcggtttt cgtttcccca ccattcaccg tctctcggtt    2760 agttttcat gcgtatccaa acacctcttt cccccttat ataaacgaca ccgtatacgc      2820
aactccatca tcgttctaaa ttaattctaa caggttcggc ataattgagc gatcgatggc    2880
ggcgttgata aggtcaccgg cggtgatact ggcgatcctg acgatctcgg cgtgcatcgc    2940
gtgtacggcg tcgtacgggg gattggtcgg gggaaggtcg aagatccctg acgtgaaggc    3000
gaacaagaag gtgcaggatc tagggcggtt ctcggtggag gagcataacc ggatgctgag    3060
gcaggcgcag aaggaggagg agcaagtcac gttcgtggaa gtggtggagg cgcaacaaca    3120
agtggtgtct gggatcaagt actacatgaa gatatcggcc acgcagggtg gcgacggtgg    3180
agattccaga atattcgaat ccgttgtggt ggtgaagccg tggcttcgtt ccaagcagct    3240
tctcaatttc gctccttcca cgcagtgaaa tacgatcaat ttcggttccg tttcaattac    3300
ttttttaact cataataaca tgcttaattg gtttagtatg ctttaatcct tctaataaaa    3360
aatatgaaag agagaaataa atgtttacaa tttctgtttc agacatgaat caactggtta    3420
acaggttaac aataatgtca aagatatatt tacattgttt tgagcatgga gtctctctat    3480
gttttttttt ttaatctact atgggcatat tttatcttag agaagtgata ctttgtacaa    3540
atatcatttc tctaactttt attatcattt ataaacgtta aacgatatta ttatgaagtt    3600
tgtctcaata aattaaaatg tttaggcgtt attaagactg gataatctag gcgtgtattc    3660
aattacgacg tttatttcgt ggacatttt tttgtctcgg gaatttattt atttttcct      3720 cataatatag catgacaatg ttattttggg gttccatata tatgctctaa aaaaattgtt    3780
tggttaatta ttaaaattga ctgtaaatgt tttttatatt ctcataaata aaacacgtgt    3840
gcttgattga gttatttttt ttgttgagag tttgattgag ttattaattt ctaactttgc    3900
ataaatgtta agtaagtttt ctatctaata acatacacat aacacctttc agtatgtaac    3960
tgagtatctt tcacgaatat atatatatat atatatatat atatatatag agagagagag    4020
agagagagag agagagagag agaagagaga gagagagaga gagagagaga gagcaattcc    4080
aatatgccta ttttgcgtga atgaaattgg cacatagga tgaaaattat ggcaaagaaa      4140
aaaaactata ttatgtaaca taaggagca ttgagggt agtaaggaga atatgtttgg        4200
atttttatga atgttgcgtg aatgaaattg gcacataaga actaaattgg tggaagaaa     4260 ctgtcacgag aataaatttt catagtttta cgttcaataa taaacagaat aacttttata    4320
gttataataa tggtagtatt aggaattatt ttagctattt ctcaacaaaa tattaagaaa    4380
attttggtct attacacgat gtctcgattg aattatatga tctaggtatg ggatgttatg    4440
gagtccgaga ttaaatatta atcctacgta aattataact tacatagaaa taaaatatgt    4500
ttaaaattaa ttattttatt acttcataat aaatatggga taaaaatttc tacctgtatt    4560
cgtgggatta caaaaattaa ttgagtaaga ccgcttctcc atctgtcatt attgaattgt    4620
tgagaagata tatacaaaat attttggtaa aaaattacag ggaataaaaa aattgtataa    4680
ggtataatac tttaatgaa agatataaga agatatttta ttgttattat ttagtcattg    4740
agtaaatttt tttttaagaa atatataagg acctcttaca atagtgcaaa tagcatttca    4800
```

```
catttgagta tagaaagtat ttcgtcaact ttttctcttc tttaaatcaa atcgtcctct    4860
agccatactt tttttatcta aaaaagttta agataaatat gaagagatct acaccaactt    4920
attaattata tttttatttt atttaaaaag ttaaaaaaaa actacagaga gacttgcctc    4980
ttattttctt ccaatataga aataagaata ataaacactc aaaagaaaaa aatattagga    5040
aaaaaatatt agaaaaaaat aagaattatt tcaggtaaat ataattttga tgtctgaaaa    5100
tgtgaaatga taacaaataa tcggatttcg aaatcaaata acgcctcatc tataaaaatg    5160
gaaatatttt gaaaaaaaaa acgttttttt tttcaaaata tttcaaaagg tacacaaaat    5220
aaataagaca attctgaagc tttttgtgca atttaatttc taattaagtt caattctcat    5280
cagtaaaaaa gtggtacacc caaaaataca gataattcgc cagctttatg tgcaatttgt    5340
gtcccattca aattatcttc aataggagtc aagggaagaa ctcaaattta gtttttaaa    5400 tataaaaaaa tataattgat tagtcatata cacaatttaa tttaatgaca aattaataca    5460 taaattttt tacacattca ttgtatttaa attttttatc tttaaacaac caataattta     5520
tttatttatt tctaagaaaa acgacaagct caatatagaa actagaaagc tcaataattt    5580
attttatcag gtacacacaa gaaccgtaca cgcgctgaca ttcaaatccc tcccatttcc    5640
caactcccaa ct                                                        5652
```

US 9,441,241 B2

METHODS AND COMPOSITIONS FOR TRANSGENIC PLANTS WITH ENHANCED RESISTANCE TO BIOTIC AND ABIOTIC STRESS

STATEMENT OF PRIORITY

This application claims the benefit, under 35 U.S.C. §119(e), of U.S. Provisional Application Ser. No. 61/761,148, filed Feb. 5, 2013, the entire contents of which are incorporated by reference herein.

STATEMENT OF GOVERNMENT SUPPORT

This invention was made with government support under grant #58-1275-353 awarded by USDA/ARS. The government has certain rights in the invention.

STATEMENT REGARDING ELECTRONIC FILING OF A SEQUENCE LISTING

A Sequence Listing in ASCII text format, submitted under 37 C.F.R. §1.821, entitled 9662-58TS_ST25.txt, 21,520 bytes in size, generated on Mar. 18, 2014 and filed via EFS-Web, is provided in lieu of a paper copy. This Sequence Listing is hereby incorporated by reference herein into the specification for its disclosures.

FIELD OF THE INVENTION

The present invention relates to methods and compositions for producing transgenic plants with enhanced resistance to pests and disease.

BACKGROUND OF THE INVENTION

Plant pests and diseases significantly decrease the quality and safety of agricultural products. In particular, insect pest control is essential for agricultural production. Insect pests cause an annual loss in food and fiber crops estimated at around $33 billion in the US alone. Yearly costs of pesticide use in the US amount to around $13 billion and yearly costs worldwide amount to around $40 billion. Despite the use of pesticides and various biological and non-chemical control measures, insect pests cause crop losses accounting for 14-15% of total production, worth over $100 billion worldwide.

One of the most destructive pests affecting soybeans worldwide is the soybean cyst nematode (SCN), which can cause more than 30% of yield loss in heavily infested fields. The annual yield losses in the US alone are about $1.5 billion.

The present invention addresses previous shortcomings in the art by providing methods and compositions to for making and using plants with enhanced resistance to pests and diseases.

SUMMARY OF THE INVENTION

In one aspect, the present invention provides a nucleic acid construct comprising a nucleotide sequence encoding GmCPI1, operably associated with a promoter. In some embodiments, the nucleotide sequence encoding GmCPI1 can be a nucleotide sequence encoding the amino acid sequence of SEQ ID NO:1 (sequence of GmCPI1 with K at position 45 as shown in FIG. 1) or a nucleotide sequence encoding the amino acid sequence of SEQ ID NO:3 (sequence of GmCPI1 with E at position 45 as shown in FIG. 1).

Also provided herein is a transformed plant cell comprising the nucleic acid construct of this invention, as well as a transgenic plant and transgenic seed comprising a nucleic acid construct of this invention.

In a further aspect, the present invention provides a method of producing transgenic plant having enhanced tolerance to biotic and/or abiotic stress, comprising: a) transforming a cell of a plant with the nucleic acid construct of this invention; and b) regenerating the transgenic plant from the transformed plant cell, wherein the plant has enhanced tolerance to biotic and/or abiotic stress as compared with a plant that is not transformed with said nucleic acid construct.

In additional aspects, the present invention provides a method of producing a transgenic plant having increased resistance to insect attack, comprising: a) transforming a cell of a plant with a nucleic acid construct of this invention; and b) regenerating the transgenic plant from the transformed plant cell, wherein the plant has increased resistance to insect attack as compared with a plant that is not transformed with said nucleic acid construct.

Additionally provided herein is a method of producing a transgenic plant having increased resistance to infection and/or disease, comprising: a) transforming a cell of a plant with a nucleic acid construct of this invention; and b) regenerating the transgenic plant from the transformed plant cell, wherein the plant has increased resistance to infection and/or disease as compared with a plant that is not transformed with said nucleic acid construct.

The present invention also provides a transgenic plant produced by the methods of this invention.

Also provided herein is a crop comprising a plurality of transgenic plants of this invention, planted together in an agricultural field, a golf course, a residential lawn, a road side, an athletic field, and/or a recreational field.

BRIEF DESCRIPTION OF THE DRAWINGS

FIG. 1. Structural features and respective amino acid sequences of cysteine protease inhibitor (CPI) protein of soybean plant Williams 82 (SEQ ID NO:1) and soybean plant PI437654 (SEQ ID NO:3). The cysteine protease inhibitor (CPI) protein contains a CY superfamily domain. A lysine in the deduced protein sequence of Williams 82 is substituted by a glutamic acid in the predicted protein sequence of PI437654.

DETAILED DESCRIPTION OF THE INVENTION

Figure 2:
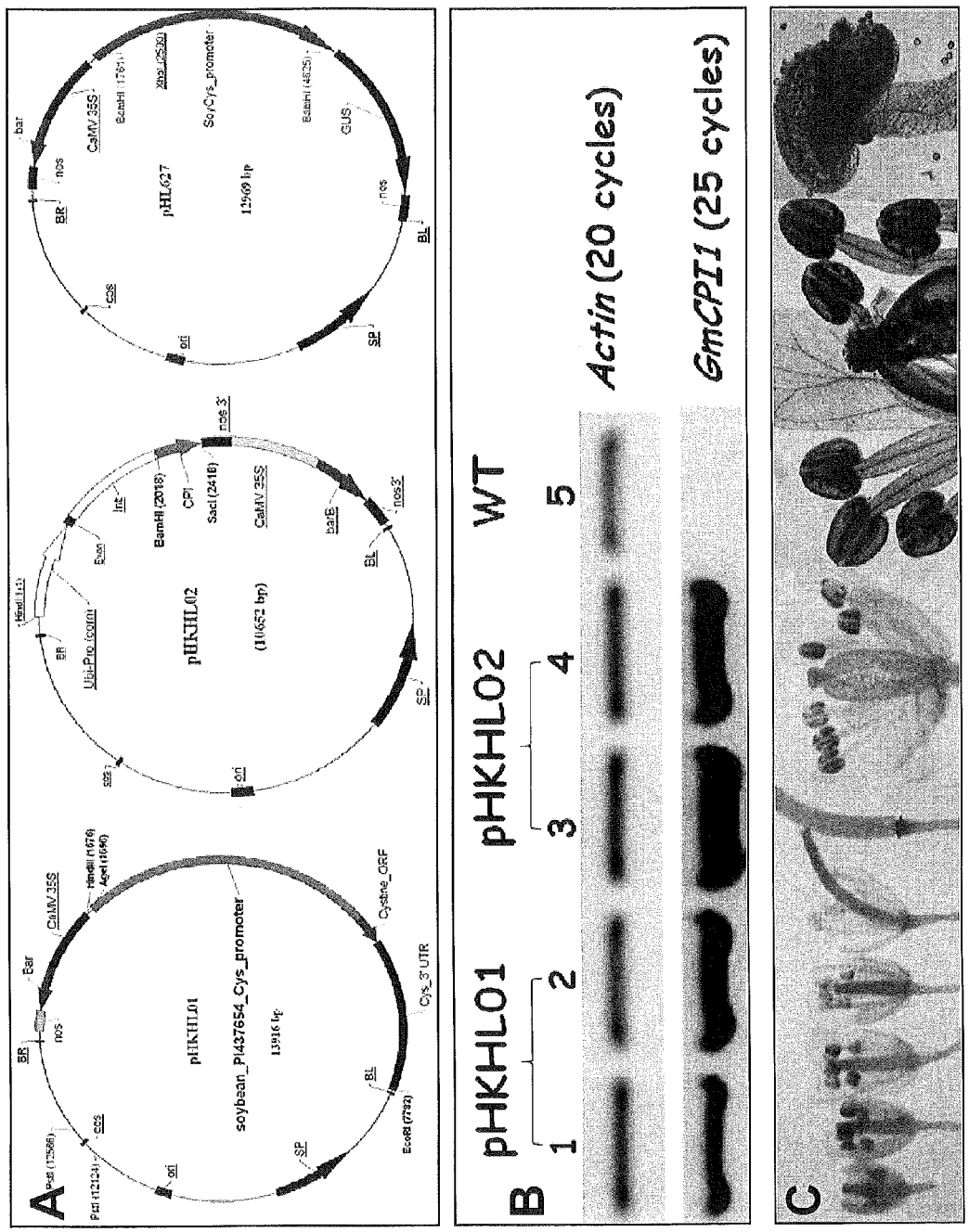
FIGS. 2A-C. Chimeric gene constructs for overexpressing GmCPI1 in transgenic plants. A. pHKHL01 is a construct comprising GmCPI1 genomic DNA of PI437654 including the GmCPI1 promoter; pHKHL02 is a construct comprising GmCPI1 cDNA of PI437654 and the corn ubiquitin promoter; and pHL627 is the construct comprising the GmCPI1 promoter and nucleotide sequence encoding GUS. B. Transgenic *Arabidopsis* plants expressing either GmCPI1 gDNA (pHKHL01) of PI437654 or cDNA (pHKHL02) of PI437654. Wild type (WT) is *Arabidopsis* that does not contain (i.e., was not transformed with) either GmCPI1 gDNA (pHKHL01) or cDNA (pHKHL02) of PI437654.

The present invention will now be described more fully hereinafter with reference to the accompanying drawings and specification, in which preferred embodiments of the invention are shown. This invention may, however, be embodied in different forms and should not be construed as limited to the embodiments set forth herein.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of dose (e.g., an amount of a non-viral vector) and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP §2111,03. Thus, the term "consisting essentially of" when used in a claim of this invention is not intended to be interpreted to be equivalent to "comprising."

The present invention is based on the unexpected discovery that the introduction into a plant of one or more of the nucleic acid constructs (e.g., isolated nucleic acid constructs) of this invention, which comprise nucleotide sequence(s) encoding the cysteine protease inhibitor, GmCPI1, results in the production of a transgenic plant having increased or enhanced resistance or tolerance to biotic and/or abiotic stress, as described herein.

Thus, in one embodiment, the present invention provides a nucleic acid construct comprising one or more (e.g., 2, 3, 4, 5, 6, 7, 8, 9, 10, etc) nucleotide sequences encoding GmCPI1 and operably associated with a promoter. The nucleic acid construct can comprise, consist essentially of and/or consist of a single nucleotide sequence encoding GmCPI1 as well as multiple nucleotide sequences encoding GmCPI1. The GmCPI1 sequences can be combined on a single construct in any combination, in any order and in any combination of multiples.

In some embodiments, the nucleotide sequence encoding GmCPI1 can be a nucleotide sequence encoding the amino acid sequence of SEQ ID NO:1 (GmCPI1 with lysine at amino acid 45 in sequence shown in FIG. 1) and in some embodiments, the nucleotide sequence encoding GmCPI1 can be a nucleotide sequence encoding the amino acid sequence of SEQ ID NO:3 (GmCP1 with glutamic acid at amino acid 45 in sequence shown in FIG. 1). In further embodiments the nucleotide sequence encoding GmCPI1 can be the nucleotide sequence of SEQ ID NO:2 and in other embodiments, the nucleotide sequence encoding GmCPI1 can be the nucleotide sequence of SEQ ID NO:4.

In still further embodiments, the nucleotide sequence encoding GmCPI1 can be a nucleotide sequence having at least about 75% identity (e.g., 75%, 76%, 77%, 78%, 79%, 80%, 81%, 82%, 83%, 84%, 85%, 86%, 87%, 88%, 89%, 90%, 91%, 92%, 93%, 94%, 95% 96,%, 97%, 98%, 99%, or 100% identity, including any fraction thereof) with the nucleotide sequence of SEQ ID NO:2 or the nucleotide sequence of SEQ ID NO:4. Furthermore, the GmCPI1 protein encoded by the nucleotide sequence of this invention can have at least about 75% identity (e.g., 75%, 76%, 77%, 78%, 79%, 80%, 81%, 82%, 83%, 84%, 85%, 86%, 87%, 88%, 89%, 90%, 91%, 92%, 93%, 94%, 95% 96,%, 97%, 98%, 99%, or 100% identity, including any fraction thereof) with the amino acid sequence of SEQ ID NO:1 or the amino acid sequence of SEQ ID NO:3.

In some embodiments, the nucleic acid construct of this invention can be pHKHL01 (as shown in FIG. 2A) and in some embodiments, the nucleic acid construct of this invention can be pHKHL02 (as shown in FIG. 2A).

In some embodiments, the nucleic acid construct of this invention can comprise consist essentially of, or consist of, in the following order from 5' to 3': a) a first promoter; b) a nucleotide sequence encoding GmCPI1 operably associated with said first promoter; and c) a first termination sequence. In further embodiments, the nucleic acid construct described herein can further comprise, consist essentially of, or consist of in the following order from 5' to 3' after the first termination sequence: d) a second promoter; e) a nucleotide sequence encoding a selectable marker operably associated with the second promoter; and f) a second termination sequence.

In some embodiments, of the nucleic acid construct described above, the first promoter can be a GmCPI1 promoter and the nucleotide sequence encoding GmCPI1 and the first termination sequence can be from a genomic GmCPI1 nucleotide sequence (e.g., the genomic nucleotide sequence encoding GMCPI1 can be isolated away from other components and materials with which it might be associated with in nature).

In some embodiments of the nucleic acid construct described above the first promoter can be heterologous to GmCPI1 and the nucleotide sequence encoding GmCPI1 can be complementary DNA (cDNA).

In particular embodiments of these nucleic acid constructs, the promoter can be a promoter that is heterologous to the GmCPI1 gene and in some embodiments, the heterologous promoter can be a corn ubiquitin promoter. As used herein, the term "promoter" refers to a region of a nucleotide sequence that incorporates the necessary signals for the efficient expression of a coding sequence. This may include sequences to which an RNA polymerase binds, but is not limited to such sequences and can include regions to which other regulatory proteins bind together with regions involved in the control of protein translation and can also include coding sequences.

Furthermore, a "promoter" or "plant promoter" of this invention is a promoter capable of initiating transcription in plant cells. Such promoters include those that drive expression of a nucleotide sequence constitutively, those that drive expression when induced, and those that drive expression in a tissue- or developmentally-specific manner, as these various types of promoters are known in the art.

Thus, for example, in some embodiments of the invention, a constitutive promoter can be used to drive the expression of a transgene of this invention in a plant cell. A constitutive promoter is an unregulated promoter that allows for continual transcription of its associated gene or coding sequence. Thus, constitutive promoters are generally active under most environmental conditions, in most or all cell types and in most or all states of development or cell differentiation.

Any constitutive promoter functional in a plant can be utilized in the instant invention. Exemplary constitutive promoters include, but are not limited to, the promoters from plant viruses including, but not limited to, the 35S promoter from CaMV (Odell et al., *Nature* 313: 810(1985)); figwort mosaic virus (FMV) 35S promoter (P-FMV35S, U.S. Pat. Nos. 6,051,753 and 6,018,100); the enhanced CaMV35S promoter (e35S); the 1'- or 2'-promoter derived from T-DNA of *Agrobacterium tumefaciens*; the nopaline synthase (NOS) and/or octopine synthase (OCS) promoters, which are carried on tumor-inducing plasmids of *Agrobacterium tumefaciens* (Ebert et al., *Proc. Natl. Acad. Sci.* (U.S.A.), 84:5745 5749, 1987); actin promoters including, but not limited to, rice actin (McElroy et al., *Plant Cell* 2: 163 (1990); U.S. Pat. No. 5,641,876); histone promoters; tubulin promoters; ubiquitin and polyubiquitin promoters, including a corn ubiquitin promoter or a rice ubiquitin promoter ((Sun and Callis, *Plant J.*, 11(5):1017-1027 (1997)); Christensen et al., *Plant Mol. Biol* 12: 619 (1989) and Christensen et al., *Plant Mol. Biol.* 18: 675(1992)); pEMU (Last et al., *Theor. Appl. Genet.* 81: 581(1991)); the mannopine synthase promoter (MAS) (Velten et al., *EMBO J.* 3: 2723(1984)); maize H3 histone (Lepelit et al., *Mol. Gen. Genet.* 231: 276 (1992) and Atanassova et al., *Plant Journal* 2: 291 (1992)); the ALS promoter, a Xbal/Ncol fragment 5' to the *Brassica napus* ALS3 structural gene (or a nucleotide sequence that has substantial sequence similarity to said Xbal/Ncol fragment); ACT11 from *Arabidopsis* (Huang et al., *Plant Mol. Biol.* 33:125-139 (1996)); Cat3 from *Arabidopsis* (GenBank No. U43147, Zhong et al., *Mol. Gen. Genet.* 251:196-203 (1996)); GPc1 from maize (GenBank No, X15596, Martinez et al., *J. Mol. Biol.* 208:551-565 (1989)); and Gpc2 from maize (GenBank No. U45855, Manjunath et al., *Plant Mol. Biol.* 33:97-112 (1997)), including any combination thereof.

In some embodiments of the present invention, an inducible promoter can be used to drive the expression of a transgene. Inducible promoters activate or initiate expression only after exposure to, or contact with, an inducing agent. Inducing agents include, but are not limited to, various environmental conditions (e.g., pH, temperature), proteins and chemicals. Examples of environmental conditions that can affect transcription by inducible promoters include pathogen attack, anaerobic conditions, extreme temperature and/or the presence of light. Examples of chemical inducing agents include, but are not limited to, herbicides, antibiotics, ethanol, plant hormones and steroids. Any inducible promoter that is functional in a plant can be used in the instant invention (see, Ward et al., (1993) *Plant Mol. Biol.* 22: 361 (1993)). Exemplary inducible promoters include, but are not limited to, promoters from the ACEI system, which respond to copper (Melt et al., *PNAS* 90: 4567 (1993)); the ln2 gene from maize, which responds to benzenesulfonamide herbicide safeners (Hershey et al., (1991) *Mol. Gen. Genetics* 227: 229 (1991) and Gatz et al., *Mol. Gen. Genetics* 243: 32 (1994)); a heat shock promoter, including, but not limited to, the soybean heat shock promoters Gmhsp 17.5-E, Gmhsp 17, 2-E and Gmhsp 17, 6-L and those described in U.S. Pat. No. 5,447,858; the Tet repressor from Tn10 (Gatz et al., *Mol. Gen. Genet.* 227: 229 (1991)) and the light-inducible promoter from the small subunit of ribulose bisphosphate carboxylase (ss-RUBISCO), including any combination thereof. Other examples of inducible promoters include, but are not limited to, those described by Moore et al. (*Plant J.* 45:651-683 (2006)). Additionally, some inducible promoters respond to an inducing agent to which plants do not normally respond. An example of such an inducible promoter is the inducible promoter from a steroid hormone gene, the transcriptional activity of which is induced by a glucocorticosteroid hormone (Schena et al., *Proc. Natl. Acad. Sci. U.S.A.* 88: 421 (1991)).

In further embodiments of the present invention, a tissue-specific promoter can be used to drive the expression of a transgene in a particular tissue in the transgenic plant. Tissue-specific promoters drive expression of a nucleic acid only in certain tissues or cell types, e.g., in the case of plants, in the leaves, stems, flowers and their various parts, roots, fruits and/or seeds, etc. Thus, plants transformed with a nucleic acid of interest operably linked to a tissue-specific promoter produce the product encoded by the transgene exclusively, or preferentially, in a specific tissue or cell type.

Any plant tissue-specific promoter can be utilized in the instant invention. Exemplary tissue-specific promoters include, but are not limited to, a root-specific promoter, such as that from the phaseolin gene (Murai et al., *Science* 23: 476 (1983) and Sengupta-Gopalan et al., *Proc. Natl. Acad. Sci. USA* 82: 3320 (1985)); a leaf-specific and light-induced promoter such as that from cab or rubisco (Simpson et al. *EMBO J.* 4: 2723 (1985) and Timko et al., *Nature* 318: 579 (1985)); the fruit-specific E8 promoter from tomato (Lincoln et al. *Proc. Nat'l. Acad. Sci. USA* 84: 2793-2797 (1988); Deikman et al. EMBO J. 7: 3315-3320 (1988); Deikman et al. *Plant Physiol.* 100: 2013-2017 (1992); seed-specific promoters of, for example, *Arabidopsis thaliana* (Krebbers et al. (1988) *Plant Physiol.* 87:859); an anther-specific promoter such as that from LAT52 (Twell et al. *Mol. Gen. Genet.* 217: 240 (1989)) or European Patent Application No 344029, and those described by Xu et al. (*Plant Cell Rep.* 25:231-240 (2006)) and Gomez et al. (*Planta* 219:967-981 (2004)); a pollen-specific promoter such as that from Zml3 (Guerrero et al., *Mol. Gen. Genet.* 224: 161 (1993)), and those described by Yamaji et al. (*Plant Cell Rep.* 25:749-57 (2006)) and Okada et al. (*Plant Cell Physiol.* 46:749-802 (2005)); a pith-specific promoter, such as the promoter isolated from a plant TrpA gene as described in International PCT Publication No. WO93/07278; and a microspore-specific promoter such as that from apg (Twell et al. *Sex. Plant Reprod.* 6: 217 (1993)). Exemplary green tissue-specific promoters include the maize phosphoenol pyruvate carboxylase (PEPC) promoter, small subunit ribulose bis-carboxylase promoters (ssRUBISCO) and the chlorophyll a/b binding protein promoters, including any combination thereof.

A promoter of the present invention can also be developmentally specific in that it drives expression during a particular "developmental phase" of the plant. Thus, such a promoter is capable of directing selective expression of a nucleotide sequence of interest at a particular period or phase in the life of a plant (e.g., seed formation), compared to the relative absence of expression of the same nucleotide sequence of interest in a different phase (e.g. seed germination). For example, in plants, seed-specific promoters are typically active during the development of seeds and germination promoters are typically active during germination of the seeds. Any developmentally-specific promoter capable of functioning in a plant can be used in the present invention.

The nucleic acid construct can further comprise one or more than one (e.g., 2, 3, 4, 5, 6, 7, 8, 9, 10, etc.) termination sequence. Nonlimiting examples of a termination sequence of this invention include the nopaline synthase (nos) sequence, gene 7 poly(A) signal, and CaMV 35S gene poly(A) signal, including any combination thereof.

The nucleic acid construct of this invention can further comprise a signal peptide sequence. Nonlimiting examples of a signal peptide sequence include the signal sequence of the tobacco AP24 protein (Coca et al. 2004); the signal peptide of divergicin A (Worobo et al. 1995); the proteinase inhibitor II signal peptide (Herbers et al. 1995); and the signal peptide from a Coix prolamin (Leite et al. 2000, Ottoboni et al. (1993), including any combination thereof.

The nucleic acid construct of this invention can further comprise a linker peptide. Nonlimiting examples of a linker peptide of this invention include the IbAMP propeptide (Francois et al. 2002, Sabelle et al. 2002); the 2A sequence of foot and mouth disease virus (Ma et al. 2002); and a serine rich peptide linker [e.g., Ser, Ser, Ser, Ser, Gly)$_y$ where y≥1 (U.S. Pat. No. 5,525,491), including any combination thereof.

The nucleic acid constructs of the present invention can further comprise a nucleotide sequence encoding a selectable marker, operably linked to a regulatory element (a promoter, for example) that allows transformed cells in which the expression product of the selectable marker sequence is produced, to be recovered by either negative selection, i.e., inhibiting growth of cells that do not contain the selectable marker, or positive selection, i.e., screening for the product encoded by the selectable marker coding sequence. For example, in one embodiment the nucleic acid construct can comprise a phosphinothricin acetyltransferase (bar) coding sequence operably associated with a rice ubiquitin promoter sequence.

Many commonly used selectable marker coding sequences for plant transformation are well known in the transformation art, and include, for example, nucleotide sequences that code for enzymes that metabolically detoxify a selective chemical agent which may be an antibiotic or a herbicide, and/or nucleotide sequences that encode an altered target which is insensitive to the inhibitor (See e.g., Aragão et al., *Braz. J. Plant Physiol.* 14: 1-10 (2002)). Any nucleotide sequence encoding a selectable marker that can be expressed in a plant is useful in the present invention.

One commonly used selectable marker coding sequence for plant transformation is the nucleotide sequence encoding neomycin phosphotransferase II (npfII), isolated from transposon Tn5, which when placed under the control of plant regulatory signals confers resistance to kanamycin (Fraley et al., *Proc. Natl. Acad Sci. U.S.A.,* 80: 4803 (1983)). Another commonly used selectable marker coding sequence encodes hygromycin phosphotransferase, which confers resistance to the antibiotic hygromycin (Vanden Elzen et al., *Plant Mol. Biol.,* 5: 299 (1985)).

Some selectable marker coding sequences confer resistance to herbicides. Herbicide resistance sequences generally encode a modified target protein insensitive to the herbicide or an enzyme that degrades or detoxifies the herbicide in the plant before it can act (DeBlock et al., *EMBO J,* 6, 2513 (1987); DeBlock et al., *Plant Physiol.* 91, 691 (1989); Fromm et al., *BioTechnology* 8, 833 (1990); Gordon-Kamm et al., *Plant Cell* 2, 603 (1990)). For example, resistance to glyphosate or sulfonylurea herbicides has been obtained using marker sequences coding for the mutant target enzymes, 5-enolpyruvylshikimate-3-phosphate synthase (EPSPS) and acetolactate synthase (ALS). Resistance to glufosinate ammonium, boromoxynil, and 2,4-dichlorophenoxyacetate (2,4-D) have been obtained by using bacterial nucleotide sequences encoding phosphinothricin acetyltransferase, a nitrilase, or a 2,4-dichlorophenoxyacetate monooxygenase, which detoxify the respective herbicides.

Other selectable marker coding sequences for plant transformation are not of bacterial origin. These coding sequences include, for example, mouse dihydrofolate reductase, plant 5-eno/pyruvylshikimate-3-phosphate synthase and plant acetolactate synthase (Eichholtz et al., *Somatic Cell Mol. Genet.* 13: 67 (1987); Shah et al., *Science* 233: 478 (1986); Charest et al., *Plant Cell Rep,* 8: 643 (1990)).

Another class of marker coding sequences for plant transformation requires screening of presumptively transformed plant cells rather than direct genetic selection of transformed cells for resistance to a toxic substance such as an antibiotic. These coding sequences are particularly useful to quantify or visualize the spatial pattern of expression of a nucleotide sequence in specific tissues and are frequently referred to as reporter nucleotide sequences because they can be fused to a gene or gene regulatory sequence for the investigation of gene expression. Commonly used nucleotide sequences for screening presumptively transformed cells include, but are not limited to, those encoding β-glucuronidase (GUS), β-galactosidase, luciferase and chloramphenicol acetyltransferase (Jefferson *Plant Mol. Biol. Rep.* 5:387 (1987); Teeri et al. *EMBO J.* 8:343 (1989); Koncz et al. *Proc. Natl. Acad. Sci. U.S.A.* 84:131 (1987); De Block et al. *EMBO J.* 3:1681 (1984)).

Some in vivo methods for detecting GUS activity that do not require destruction of plant tissue are available (e.g., Molecular Probes Publication 2908, Imagene Green™, p. 1-4 (1993) and Naleway et al., *J. Cell Biol.* 115:15 (1991)). In addition, a nucleotide sequence encoding green fluorescent protein (GFP) has been utilized as a marker for expression in prokaryotic and eukaryotic cells (Chalfie et al., *Science* 263:802 (1994)). GFP and mutants of GFP may be used as screenable markers. Similar to GFP, red fluorescent protein (DsRed2) has also been used as a selectable marker in plants (Nishizawa et al., *Plant Cell Reports* 25 (12): 1355-1361 (2006)). In addition, reef coral proteins have been used as selectable markers in plants (Wenck et al. *Plant Cell Reports* 22(4):244-251 (2003)).

For purposes of the present invention, selectable marker coding sequences can also include, but are not limited to, nucleotide sequences encoding: neomycin phosphotransferase I and II (Southern et al., *J. Mol. Appl. Gen.* 1:327 (1982)); Fraley et al., *CRC Critical Reviews in Plant Science* 4:1 (1986)); cyanamide hydratase (Maier-Greiner et al., *Proc. Natl. Acad. Sci. USA* 88:4250 (1991)); aspartate kinase; dihydrodipicolinate synthase (Perl et al., *BioTechnology* 11, 715 (1993)); bar gene (Told et al., *Plant Physiol.* 100:1503 (1992); Meagher et al., *Crop Sci.* 36:1367 (1996)); tryptophane decarboxylase (Goddijn et al., *Plant Mol. Biol.* 22:907 (1993)); hygromycin phosphotransferase (HPT or HYG; Shimizu et al., *Mol. Cell. Biol.* 6:1074 (1986); Waldron et al., *Plant Mol. Biol.* 5:103 (1985); Zhijian et al., *Plant Science* 108:219 (1995)); dihydrofolate reductase (DHFR; Kwok et al., *Proc. Natl. Acad. Sci. USA* 83:4552 (1986)); phosphinothricin acetyltransferase (DeBlock et al., *EMBO J.* 6:2513 (1987)); 2,2-dichloropropionic acid dehalogenase (Buchanan-Wollatron et al., *J. Cell. Biochem.* 13D:330 (1989)); acetohydroxyacid synthase (U.S. Pat. No. 4,761,373 to Anderson et al.; Haughn et al., *Mol. Gen. Genet.* 221:266 (1988)); 5-enolpyruvyl-shikimate-phosphate synthase (aroA; Comai et al., *Nature* 317:741 (1985)); haloarylnitrilase (PCT Publication No. WO 87/04181 to Stalker et al.); acetyl-coenzyme A carboxylase (Parker et al., *Plant Physiol,* 92:1220 (1990)); dihydropteroate synthase (su/I; Guerineau et al., *Plant Mol. Biol.* 15:127 (1990)); and 32 kDa photosystem II polypeptide (psbA; Hirschberg et al., *Science* 222:1346 (1983)).

Also included are nucleotide sequences that encode polypeptides that confer resistance to: gentamicin (Miki et al., *J. Biotechnol.* 107:193-232 (2004)); chloramphenicol (Herrera-Estrella et al., *EMBO J.* 2:987 (1983)); methotrexate (Herrera-Estrella et al., *Nature* 303:209 (1983); Meijer et al., *Plant Mol. Biol.* 16:807 (1991)); Meijer et al., *Plant Mol. Bio.* 16:807 (1991)); streptomycin (Jones et al. *Mol. Gen. Genet.* 210:86 (1987)); spectinomycin (Bretagne-Sagnard et al. *Transgenic Res.* 5:131 (1996)); bleomycin (Hille et al. *Plant Mol. Biol.* 7, 171 (1986)); sulfonamide (Guerineau et al. *Plant Mol. Bio.* 15:127 (1990)); bromoxynil (Stalker et al. *Science* 242:419 (1988)); 2,4-D (Streber et al. *Bio/Technology* 7, 811 (1989)); phosphinothricin (DeBlock et al. *EMBO J.* 6:2513 (1987)); and/or spectinomycin (Bretagne-Sagnard and Chupeau, *Transgenic Research* 5:131 (1996)).

The product of the bar gene confers herbicide resistance to glufosinate-type herbicides, such as phosphinothricin (PPT) or bialaphos, and the like. As noted above, other selectable markers that could be used in the nucleic acid constructs of the present invention include, but are not limited to, the pat gene or coding sequence, the expression of which also confers resistance to bialaphos and phosphinothricin resistance, the ALS gene or coding sequence for imidazolinone resistance, the HPH or HYG gene or coding sequence for hygromycin resistance (Coca et al. 2004), the EPSP synthase gene or coding sequence for glyphosate resistance, the Hm1 gene or coding sequence for resistance to the Hc-toxin, a coding sequence for streptomycin phosphotransferase resistance (Mazodier et al.) and/or other selective agents used routinely and known to one of ordinary skill in the art. See generally, Yarranton, *Curr. Opin. Biotech.* 3:506 (1992); Chistopherson et al., *Proc. Natl. Acad. Sci. USA* 89:6314 (1992); Yao et al., *Cell* 71:63 (1992); Reznikoff, *Mol. Microbiol.* 6:2419 (1992); Barkley et al., *The Operon* 177-220 (1980); Hu et al., *Cell* 48:555 (1987); Brown et al., *Cell* 49:603 (1987); Figge et al., *Cell* 52:713 (1988); Deuschle et al., *Proc. Natl. Acad. Sci. USA* 86:400 (1989); Fuerst et al., *Proc. Natl. Acad. Sci. USA* 86:2549 (1989); Deuschle et al., *Science* 248:480 (1990); Labow et al., *Mol. Cell. Biol.* 10:3343 (1990); Zambretti et al. *Proc. Natl. Acad. Sci. USA* 89:3952 (1992); Baim et al., *Proc. Natl. Acad. Sci. USA* 88:5072 (1991); Wyborski et al., *Nuc. Acids Res.* 19:4647 (1991); Hillenand-Wissman, *Topics in Mol. And Struc. Biol.* 10:143 (1989); Degenkolb et al., *Antimicrob. Agents Chemother.* 35:1591 (1991); Kleinschnidt et al., *Biochemistry* 27:1094 (1988); Gatz et al., *Plant J.* 2:397 (1992); Gossen et al., *Proc. Natl. Acad. Sci. USA* 89:5547 (1992); Oliva et al., *Antimicrob. Agents Chemother.* 36:913 (1992); Hlavka et al., *Handbook of Experimental Pharmacology* 78 (1985); and Gill et al., *Nature* 334:721 (1988). A review of approximately 50 marker genes in transgenic plants is provided in Miki et al. (2003), the entire contents of which are incorporated by reference herein.

Additionally, for purposes of the present invention, selectable markers include nucleotide sequence(s) conferring environmental or artificial stress resistance or tolerance including, but not limited to, a nucleotide sequence conferring high glucose tolerance, a nucleotide sequence conferring low phosphate tolerance, a nucleotide sequence conferring mannose tolerance, and/or a nucleotide sequence conferring drought tolerance, salt tolerance or cold tolerance. Examples of nucleotide sequences that confer environmental or artificial stress resistance or tolerance include, but are not limited to, a nucleotide sequence encoding trehalose phosphate synthase, a nucleotide sequence encoding phosphomannose isomerase (Negrotto et al., *Plant Cell Reports* 19(8):798-803 (2003)), a nucleotide sequence encoding the *Arabidopsis* vacuolar $H^+$-pyrophosphatase gene, AVP1, a nucleotide sequence conferring aldehyde resistance (U.S. Pat. No. 5,633,153), a nucleotide sequence conferring cyanamide resistance (Weeks et al., *Crop Sci* 40:1749-1754 (2000)) and those described by Iuchi et al. (*Plant J.* 27(4):325-332 (2001)); Umezawa et al. (*Curr Opin Biotechnol.* 17(2):113-22 (2006)); U.S. Pat. No. 5,837,545; Oraby et al. (*Crop Sci.* 45:2218-2227 (2005)) and Shi et al. (*Proc. Natl. Acad. Sci.* 97:6896-6901 (2000)).

The above list of selectable marker genes and coding sequences is not meant to be limiting as any selectable marker coding sequence now known or later identified can be used in the present invention. Also, a selectable marker of this invention can be used in any combination with any other selectable marker.

In some embodiments of this invention, the nucleic acid construct of this invention can comprise gene elements to control gene flow in the environment in which a transgenic plant of this invention could be placed. Examples of such elements are described in International Publication No. WO 2009/011863, the disclosures of which are incorporated by reference herein.

In some embodiments, the nucleic acid construct of this invention can comprise elements to impart sterility to the transgenic plant into which the nucleic acid construct is introduced in order to control movement of the transgene(s) of this invention in the environment. As one example, RNAi technology can be used to turn off the expression of certain endogenous genes, resulting in a plant that maintains vegetative growth during its whole life cycle. In particular examples the LFY gene of *Arabidopsis* and the FLO/LFY homolog in creeping bentgrass can be targeted by interfering RNA molecules according to well known techniques to inhibit expression of these genes in the transgenic plant and producing sterility in the transgenic plant.

Elements that can impart sterility to the transgenic plant include, but are not limited to, nucleotide sequences, or fragments thereof, that modulate the reproductive transition from a vegetative meristem or flower promotion gene or coding sequence, or flower repressor gene or coding sequence. Three growth phases are generally observed in the life cycle of a flowering plant: vegetative, inflorescence and floral. The switch from vegetative to reproductive or floral growth requires a change in the developmental program of the descendents of the stem cells in the shoot apical meristem. In the vegetative phase, the shoot apical meristem generates leaves that provide resources necessary to produce fertile offspring. Upon receiving the appropriate environmental and developmental signals, the plant switches to floral (reproductive) growth and the shoot apical meristem enters the inflorescence phase, giving rise to an inflorescence with flower primordia. During this phase, the fate of the shoot apical meristem and the secondary shoots that arise in the axils of the leaves is determined by a set of meristem identity genes, some of which prevent and some of which promote the development of floral meristems. Once established, the plant enters the late inflorescence phase where the floral organs are produced. Two basic types of inflorescences have been identified in plants: determinate and indeterminate. In a species producing a determinate inflorescence, the shoot apical meristem eventually produces floral organs and the production of meristems is terminated with a flower. In those species producing an indeterminate inflorescence, the shoot apical meristem is not converted to a floral identity and therefore only produces floral meristems from its periphery, resulting in a continuous growth pattern.

In dicots, after the transition from vegetative to reproductive development, floral meristems are initiated by the action of a set of genes called floral meristem identity genes. FLORICAULA (flo) of *Antirrhinum* and its *Arabidopsis* counterpart, LEAFY (lfy), are floral meristems identity genes that participate in the reproductive transition to establish floral fate. In strong flo and lfy mutant plants, flowers are transformed into inflorescence shoots (Coen et al., *Cell* 63:1311-1322 (1990); Weigel et al. *Cell* 69:843-859, (1992)), indicating that flo and lfy are exemplary flower-promotion genes.

In monocots, FLO/LFY homologs have been identified in several species, such as rice (Kyozuka et al., *Proc. Natl. Acad. Sci.* 95:1979-1982 (1998)); *Lolium temulentum*, maize, and ryegrass (*Lolium perenne*). The FLO/LFY homologs from different species have high amino acid sequence homology and are well conserved in the C-terminal regions (Kyozuka et al., *Proc. Natl. Acad. Sci.* 95:1979-1982 (1998); Bomblies et al., *Development* 130:2385-2395 (2003)).

In addition to flo/lfy genes or coding sequences, other examples of flower promotion genes or coding sequences include, but are not limited to, APETALA1 (Accession no. NM105581)/SQUAMOSA (ap1/squa) in *Arabidopsis* and *Antirrhinum*, CAULIFLOWER (cal, Accession no. AY174609), FRUITFUL (ful, Accession no. AY173056), FLOWERING LOCUS T (Accession no. AB027505), and SUPPRESSOR OF OVEREXPRESSION OF CONSTANS1 (soc1) in *Arabidopsis* (Samach et al., *Science* 288:1613-1616 (2000); Simpson and Dean, *Science* 296:285-289 (2002)); Zik et al., *Annu. Rev. Cell Dev. Biol.* 19:119-140 (2003)).

Additional non-limiting examples of flowering related genes or coding sequences include TERMINAL FLOWER 1 (tfl1) in *Arabidopsis* and its homolog CENTRORADIALS (cen) in *Antirrhinum*; FLOWERING LOCUS C (flc) and the emf gene in *Arabidopsis*. It is noted that any flower-promotion or flower-related coding sequence(s), the down-regulation of which results in no or reduced sexual reproduction (or total vegetative growth), can be used in the present invention.

Down-regulation of expression of one or more flower promotion or coding sequences in a plant, such as a flo/lfy homolog, results in reduced or no sexual reproduction or total vegetative growth in the transgenic plant, whereby the transgenic plant is unable to produce flowers (or there is a significant delay in flower production). The high conservation observed among flo/lfy homologs indicates that further flo/lfy homologs can be isolated from other plant species by using, for example, the methods of Kyozuka et al. (*Proc. Natl. Acad. Sci.* 95:1979-1982 (1998)) and Bomblies et al. (*Development* 130:2385-2395 (2003)). For example, the flo/lfy homolog from bentgrass (*Agrostis stolonifera* L.) has been cloned (U.S. Patent Publication No. 2005/0235379).

Accordingly, in some embodiments of the present invention, RNAi technology can be used to turn off the expression of one or more endogenous genes involved in the transition from a vegetative to a reproductive growth stage, as set forth above.

Nucleic acids of this invention can comprise a nucleotide sequence that can be identical in sequence to the sequence which is naturally occurring or, due to the well-characterized degeneracy of the nucleic acid code, can include alternative codons that encode the same amino acid as that which is found in the naturally occurring sequence. Furthermore, nucleic acids of this invention can comprise nucleotide sequences that can include codons which represent conservative substitutions of amino acids as are well known in the art, such that the biological activity of the resulting polypeptide and/or fragment is retained. A nucleic acid of this invention can be single or double stranded. Additionally, the nucleic acids of this invention can also include a nucleic acid strand that is partially complementary to a part of the nucleic acid sequence or completely complementary across the full length of the nucleic acid sequence.

Also as used herein, the terms "nucleic acid," "nucleic acid molecule," "nucleotide sequence," "oligonucleotide" and "polynucleotide" can be used interchangeably to refer to a heteropolymer of nucleotides and encompass both RNA and DNA, including cDNA, genomic DNA, mRNA, a DNA fragment, genomic DNA, synthetic (e.g., chemically synthesized) DNA, plasmid DNA, siRNA, miRNA, anti-sense RNA and chimeras of RNA and DNA, any of which can be single stranded or double stranded.

The term polynucleotide, nucleotide sequence, or nucleic acid refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present invention further provides a nucleic acid that is the complement (which can be either a full complement or a partial complement) of a nucleic acid, nucleotide sequence, or polynucleotide of this invention. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§1.821-1.825 and the World Intellectual Property Organization (WIPO) Standard ST.25.

In some embodiments, the recombinant nucleic acids molecules, nucleotide sequences and polypeptides of the invention are "isolated." An "isolated" nucleic acid molecule, an "isolated" nucleotide sequence or an "isolated" polypeptide is a nucleic acid molecule, nucleotide sequence or polypeptide that, by the hand of man, exists apart from its native environment and is therefore not a product of nature. An isolated nucleic acid molecule, nucleotide sequence or polypeptide may exist in a purified form that is at least partially separated from at least some of the other components of the naturally occurring organism or virus, for example, the cell or viral structural components or other polypeptides or nucleic acids commonly found associated with the polynucleotide. In representative embodiments, the isolated nucleic acid molecule, the isolated nucleotide sequence and/or the isolated polypeptide is at least about 1%, 5%, 10%, 20%, 30%, 40%, 50%, 60%, 70%, 80%, 90%, 95%, or more pure.

In other embodiments, an isolated nucleic acid molecule, nucleotide sequence or polypeptide may exist in a non-native environment such as, for example, a recombinant host cell. Thus, for example, with respect to nucleotide sequences, the term "isolated" means that it is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, the recombinant nucleic acid molecules, nucleotide sequences and their encoded polypeptides are "isolated" in that, by the hand of man, they exist apart from their native environment and therefore are not products of nature, however, in some embodiments, they can be introduced into and exist in a recombinant host cell.

In some embodiments, the nucleotide sequences and/or nucleic acid molecules of the invention can be operatively associated with a variety of promoters for expression in host cells (e.g., plant cells). As used herein, "operatively associated with," when referring to a first nucleic acid sequence that is operatively linked to a second nucleic acid sequence, means a situation when the first nucleic acid sequence is placed in a functional relationship with the second nucleic acid sequence. For instance, a promoter is operatively associated with a coding sequence if the promoter effects the transcription or expression of the coding sequence.

As used herein, the term "gene" refers to a nucleic acid molecule capable of being used to produce mRNA or antisense RNA. Genes may or may not be capable of being used to produce a functional protein. Genes include both coding and non-coding regions (e.g., introns, regulatory elements, promoters, enhancers, termination sequences and 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

An "isolated" nucleic acid of the present invention is generally free of nucleic acid sequences that flank the nucleic acid of interest in the genomic DNA of the organism from which the nucleic acid was derived (such as coding sequences present at the 5' or 3' ends). However, the nucleic acid of this invention can include some additional bases or moieties that do not deleteriously affect the basic structural and/or functional characteristics of the nucleic acid. "Isolated" does not mean that the preparation is technically pure (homogeneous).

The term "transgene" as used herein, refers to any nucleic acid sequence used in the transformation of a plant or other organism. Thus, a transgene can be a coding sequence, a non-coding sequence, a cDNA, a gene or fragment or portion thereof, a genomic sequence, a regulatory element and the like.

The term "antisense" or "antigene" as used herein, refers to any composition containing a nucleotide sequence that is either fully or partially complementary to, and hybridize with, a specific DNA or RNA sequence. The term "antisense strand" is used in reference to a nucleic acid strand that is complementary to the "sense" strand. Antisense molecules include peptide nucleic acids (PNAs) and may be produced by any method including synthesis, restriction enzyme digestion and/or transcription. Once introduced into a cell, the complementary nucleic acid sequence combines with nucleic acid sequence(s) present in the cell (e.g., as an endogenous or exogenous sequence(s)) to form a duplex thereby preventing or minimizing transcription and/or translation. The designation "negative" is sometimes used in reference to the antisense strand, and "positive" is sometimes used in reference to the sense strand. An antigene sequence can be used to form a hybridization complex at the site of a noncoding region of a gene, thereby modulating expression of the gene or coding sequence (e.g., by enhancing or repressing transcription of the gene or coding sequence).

The term "RNAi" refers to RNA interference. The process involves the introduction of RNA into a cell that inhibits the expression of a gene. Also known as RNA silencing, inhibitory RNA, and RNA inactivation. RNAi as used herein includes double stranded (dsRNA), small interfering RNA (siRNA), small hairpin RNA (or short hairpin RNA) (shRNA) and microRNA (miRNA).

The terms "complementary" or "complementarity," as used herein, refer to the natural binding of polynucleotides under permissive salt and temperature conditions by base-pairing. For example, the sequence "A-G-T" binds to the complementary sequence "T-C-A." Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins.

Thus, the compositions and methods of the invention further comprise homologues to the nucleotide sequences and polypeptide sequences of this invention (e.g., SEQ ID NO:1, SEQ ID NO:2, SEQ ID NO:3, SEQ ID NO:4, SEQ ID NO:5, etc.). "Orthologous," as used herein, refers to homologous nucleotide sequences and/or amino acid sequences in different species that arose from a common ancestral gene during speciation. A homologue of this invention has a significant sequence identity (e.g., 70%, 75%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to SEQ ID NO:1, SEQ ID NO:2, SEQ ID NO:3, SEQ ID NO:4, SEQ ID NO:5, SEQ ID NO:6, SEQ ID NO:7 or SEQ ID NO:8.

As used herein "sequence identity" or "identity" refers to the extent to which two optimally aligned polynucleotide or peptide sequences are invariant throughout a window of alignment of components, e.g., nucleotides or amino acids. An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence. As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). In some embodiments, "percent identity" can refer to the percentage of identical amino acids in an amino acid sequence.

Optimal alignment of, sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

The percent of sequence identity can be determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *J. Mol. Biol.* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Adv. Appl. Math.*, 2:482-489, 1981, Smith et al., *Nucleic Acids Res.* 11:2205-2220, 1983).

Useful methods for determining sequence identity are also disclosed in *Guide to Huge Computers* (Martin J. Bishop, ed., Academic Press, San Diego (1994)), and Carillo and Lipton (*Applied Math* 48:1073(1988)). More particularly, preferred computer programs for determining sequence identity include but are not limited to the Basic Local Alignment Search Tool (BLAST®) software programs which are publicly available from the National Center for Biotechnology Information (NCBI) at the National Library of Medicine, National Institute of Health, Bethesda, Md. 20894; see BLAST® Software Manual, Altschul et al., NCBI, NLM, NIH; (Altschul et al., *J. Mol. Biol.* 215:403-410 (1990)); version 2.0 or higher of BLAST® software programs allows the introduction of gaps (deletions and insertions) into alignments; for peptide sequence, BLASTX® software program can be used to determine sequence identity; and, for polynucleotide sequence, BLASTN® software program can be used to determine sequence identity.

The elements of the nucleic acid constructs of the present invention can be in any combination. Thus, in the nucleic acid constructs described herein, the respective elements can be present in the order described and immediately adjacent to the next element upstream and/or downstream, with no intervening elements and/or the respective elements can be present in the order described and intervening elements can be present between the elements, in any combination.

In addition, in the constructs of this invention that recite multiple elements of the same name (e.g., a first promoter and a second promoter or a first termination sequence and a second termination sequence or a first nucleotide sequence encoding GmCPI1 and a second nucleotide sequence encoding GmCPI1) in a single construct, such similarly named elements can be the same or they can be different in any combination (e.g., a first promoter sequence can be a corn ubiquitin promoter sequence and a second promoter sequence can be rice ubiquitin promoter sequence or a first termination sequence can be nos and a second termination sequence can also be nos).

The present invention further provides a transformed plant cell comprising the nucleic acid construct or a multiplicity of different nucleic acid constructs of this invention, in any combination. Furthermore, the elements of the nucleic acid constructs transformed into the plant cell can be in any combination.

A transgenic plant is also provided herein, comprising, consisting essentially of and/or consisting of one or more nucleic acid constructs of this invention. A transgenic plant is additionally provided herein comprising a transformed plant cell of this invention.

Additionally provided herein is a transgenic seed, a transgenic pollen grain and a transgenic ovule of the transgenic plant of this invention, wherein the seed, pollen grain and ovule comprise a heterologous nucleic acid construct of this invention. Further provided is a tissue culture of regenerable transgenic cells of the transgenic plant of this invention.

A plant of this invention can be an angiosperm, a gymnosperm, a bryophyte, a fern and a fern ally. In some embodiments the plant is a dicot and in some embodiments, the plant is a monocot. In some embodiments, the plant of this invention is a crop plant.

Nonlimiting examples of a plant of this invention include, turfgrass (e.g., creeping bentgrass, tall fescue, ryegrass), forage grasses (e.g., *Medicago truncatula*, alfalfa), switchgrass, trees (e.g., orange, lemon, peach, apple, plum, poplar, coffee), tobacco, tomato, potato, sugar beet, pea, green bean, lima bean, carrot, celery, cauliflower, broccoli, cabbage, soybean, oil seed crops (e.g., canola, sunflower, rapeseed), cotton, *Arabidopsis*, pepper, peanut, grape, orchid, rose, dahlia, carnation, cranberry, blueberry, strawberry, lettuce, cassava, spinach, lettuce, cucumber, zucchini, wheat, maize, soybean, rye, rice, flax, oat, barley, *sorghum*, millet, sugarcane, peanut, beet, potato, sweetpotato, banana, and the like.

The present invention also provides a crop comprising a plurality of transgenic plants of this invention, planted together in an agricultural field, a golf course, a residential lawn, a road side, an athletic field, and/or a recreational field.

In an embodiment of this invention, a method is provided of producing transgenic plant having enhanced tolerance to biotic and/or abiotic stress, comprising: a) transforming a cell of a plant with one or more than one (e.g., 2, 3, 4, 5, 6, 7, 8, 9, 10, etc.) nucleic acid construct of this invention; and b) regenerating the transgenic plant from the transformed plant cell, wherein the plant has enhanced tolerance to biotic and/or abiotic stress as compared with a plant that is not transformed with said nucleic acid construct. In some embodiments, the stress can be biotic stress, which can, in some embodiments, be insect damage. In some embodiments, the stress can be abiotic stress, which can, in some embodiments, be salt stress and/or drought stress.

By increased or enhanced tolerance or increased or enhanced resistance as used herein, it is meant that the transgenic plant of this invention that has been transformed with a nucleic acid construct of this invention has a tolerance or resistance to a biotic and/or abiotic stress that is greater than (e.g., by at least about 2%, 5%, 10%, 20%, 30%, 40%, 50%, 60%, 70%, 80%, 90%, 100% or more) the tolerance or resistance to the biotic and/or abiotic stress demonstrated or observed in a control plant (e.g., a plant that has not been transformed with the nucleic acid construct of this invention)

Nonlimiting examples of biotic stress include insect attack, which includes but is not limited to, insect infestation, insect infection, insect damage, disease caused by contact with insects and any combination thereof. Biotic stress also includes infection, disease, toxicity and/or damage caused by plant pathogens.

Nonlimiting examples of the types of insects against which a transgenic plant of this invention can have increased or enhanced resistance include, for example, all species of thrips in the Merothripidae family, all species of nematodes in the phylum Nematoda, all species of aphids in the Aphidoidea family, all species of spider mites in the Tetranychidae family, and all species of whiteflies in the Aleyrodidae family.

Nonlimiting examples of the types of plant pathogens against which a transgenic plant of this invention can have increased or enhanced resistance include plant pathogenic fungi, plant pathogenic bacteria, plant pathogenic viruses, plant pathogenic nematodes, plant pathogenic spiroplasmas and mycoplasma-like organisms and plant pathogenic water molds. Nonlimiting examples of a fungal pathogen against which a transgenic plant of this invention can have increased or enhanced resistance include *Alternaria* spp. (e.g. *A. longipes, A. alternata, A. solani, A. dianthi*), *Botrytis* spp. (e.g., *B. cinerea, B. tulipae, B. aclada, B. anthophila, B. elliptica*), *Cercospora* spp. (e.g., *C. asparagi, C. brassicicola C. apii*), *Claviceps* spp. (*C. purpurea, C. fusiformis*), *Cladosporium* spp. (e.g., *C. sphaerospermum, C. fulvum, C. cucumerinum*), *Fusarium* spp. (e.g., *F. oxysporum, F. moniliforme, F. solani, F. culmorum, F. graminearum*), *Helminthosporium* spp. (e.g., *H. solani, H. oryzae, H. Victoriae*), *Cochliobolus* spp., *Dreschlera* spp., *Penicillium* spp. (e.g., *P. digitatum, P. expansum*), *Trichoderma* spp. (*T. viride, T. hamatum*), *Verticillium* spp. (e.g., *V. alboatrum, V. dahliae, V. fungicola*), *Colletotrichum* spp. (e.g., *C. gloeosporioides, C. lagenarium, C. coccodes, C. orbiculare*), *Gloeodes* spp. (e.g., *G. Pomigena*), *Glomerella* spp. (e.g., *G. cingulata, G. glycines*), *Gloeosporium solani, Marssonina* spp. (e.g., *M. populi*), *Nectria* spp. (e.g, *N. galligena, N. cinnabarina*), *Phialophora malorum, Sclerotinia* spp. (e.g., *S. sclerotiorum, S. trifoliorum*), *Magneporthe* spp. (e.g., *M. grisea, M. salvinii*), *Rhizoctonia* spp. (*R. Solani*), *Mycosphaerella* spp. (e.g., *M. fijiensis, M. dianthi, M. citri, M. graminicola*), *Ustilago* spp. (e.g., *U. maydis*)

Nonlimiting examples of a bacterial pathogen against which a transgenic plant of this invention can have increased or enhanced resistance include *Pseudomonas* spp (e.g., *P. syringae, P. syringae* pv. *Tabaci, P. marginata*), *Erwinia* spp. (*E. carotovora, E. amylovora*), *Xanthomonas* spp., and *Agrobacterium* spp. (*A. tumefaciens, A. rhizogenes*), and the like.

Nonlimiting examples of a water mold against which a transgenic plant of this invention can have increased or enhanced resistance include *Pythium* spp. (*P. aphanidermatum, P. graminicola, P. ultimatum*), *Phytophthora* spp. (e.g., *P. citrophthora, P. infestans, P. cinnamomi, P. megasperma, P. syringae*).

Nonlimiting examples of a nematode against which a transgenic plant of this invention can have increased or enhanced resistance include *Xiphenema* spp. (*X. america-* num), *Pratylenchus* spp. (*P. neglectus, P. thornei*), *Paratylenchus* spp. (*P. bukowinensis*), *Criconemella* spp. (*C. xenoplax, C. curvata; C, ornata*), *Meloidogyne* spp. (*M. incognita, M. graminicola, M. arenaria*), *Helicotylenchus* spp. (*H. dihystera, H. multicinctus*), *Rotylenchulus* spp., *Longidorus* spp., *Heterodera* spp. (*H. glycines, H. zeae, H. schachtii*), *Anguina* spp. (*A. agrostis, A. triad*), *Tylenchulus* spp. (*T. semipenetrans*). A particular example of a nematode that can infect a plant of this invention is soybean cyst nematode (SCN; *Heterodera glycines*). In the examples provided herein, it has been shown that overexpression of GmCPI1 of PI437654 in a transgenic soybean plant that has been transformed with a nucleic acid construct of this invention enhances resistance to SCN infection as compared to a plant that has not been transformed with the nucleic acid construct of this invention.

Nonlimiting examples of a virus against which a transgenic plant of this invention can have increased or enhanced resistance include Rhabdovirus, Alfamovirus, Tobomovirus, Luteovirus, Potyvirus, Cucumovirus, Nepovirus, Comoviridae, Sobemovirus, Carlavirus, Ilarvirus, Potexvirus, Caulimovirus, and Geminivirus. Further nonlimiting examples of a virus which a transgenic plant of this invention can have increased or enhanced resistance include tomato spotted wilt virus, tobacco rattle virus, tobacco necrosis virus, tobacco ring spot virus, tomato ring spot virus, cucumber mosaic virus, peanut stump virus, alfalfa mosaic virus, maize streak virus, figwort mosaic virus, tomato golden mosaic virus, tomato mottle virus, tobacco mosaic virus, cauliflower mosaic virus, tomato yellow leaf curl virus, tomato leaf curl virus, potato yellow mosaic virus, African cassava mosaic virus, Indian cassava mosaic virus, bean golden mosaic virus, bean dwarf mosaic virus, squash leaf curl virus, cotton leaf curl virus, beet curly top virus, Texas pepper virus, Pepper Huastico virus, alfalfa mosaic virus, bean leaf roll virus, bean yellow mosaic virus, cucumber mosaic virus, pea streak virus, tobacco streak virus, and white clover mosaic virus.

Nonlimiting examples of a *spiroplasma* or mycoplasma-like organism which a transgenic plant of this invention can have increased or enhanced resistance include *Phytoplasma* spp. (*P. oryzae, P. solani, P. trifolii, P. ulmi*) and *Spiroplasma* spp.

Nonlimiting examples of a disease against which a transgenic plant of this invention can have increased or enhanced resistance include, for example, bacterial canker (pathogen: *Clavibacter* or *Pseudomonas*, leads to plant leaf yellowing, wilting, stem browning, fruit spotting, or necrotic spots), bacterial wilt disease (pathogen: *Ralstonia* genus, leads to plant wilt, bacterial ooze in stem, stem browning), basal stem rot (pathogen: *Sclerotium* genus, leads to plant mall brown round sclerotia and white mycelium on stem base), blight (pathogen: *Alternaria, Colletotrichum* genus, leads to concentric circular black lesions on plant leaves, brown-white tip), common smut (pathogen: *Ustilago* genus, leads to large white galls replacing kernels, black spore masses; can also infect the tassel and stalk), crown rot (pathogen: *Aspergillus* genus, leads to plant stunting and wilting), *Fusarium* wilt (pathogen: *Fusarium* genus, leads to plant wilt, vascular stem browning), late blight (pathogen: *Phytophthora* genus, leads to plant grey fungal growth on underside of leaf), leaf mould (pathogen: *Cladosporium* genus, leads to grey/purple fungal growth on leaf underside), powdery mildew (pathogen: in the order of Erysiphales), nematode infection or infestation (pathogen: *Meloidogyne* genus, leads to plant wilt, galls on roots), rust (pathogen: *Puccinia*, leads to reddish rust pustules on leaves), wilt virus (pathogen: virus, leads to small areas browning on young leaves, dark spots or rings on old leaves) and yellow top virus (pathogen: virus, leads to small yellow curled leaves).

Nonlimiting examples of abiotic stress include drought stress, salt stress, heat stress, cold stress, oxidative stress, phosphate deficiency, flowering, abscisic acid signaling, salicylic acid signaling and any combination thereof.

Additional embodiments of this invention include methods of producing a transgenic plant and the plants produced according to the methods described herein.

Thus, the present invention provides a method of producing a transgenic plant having increased resistance to insect infestation, attack and/or damage, comprising: a) transforming a cell of a plant with one or more (e.g., 2, 3, 4, 5, 6, etc.) of the nucleic acid constructs of this invention; and b) regenerating the transgenic plant from the transformed plant cell, wherein the plant has increased resistance to insect infestation, attack and/or damage as compared with a plant that is not transformed with said nucleic acid construct. In situations in which the standard or routine procedure would be to contact a plant with an insecticide and/or other insect barrier to protect the plant from insect attack and/or damage, the use of a transgenic plant would be expected to reduce or eliminate the need for an insecticide. Thus, in some embodiments, the transgenic plant of this invention is a plant that is not and/or does not need to be contacted with an insecticide or other insect barrier to protect the plant from insect attack and/or damage.

The present invention further provides a method of producing a transgenic plant having increased resistance to infection and/or disease, comprising: a) transforming a cell of a plant with one or more (e.g., 2, 3, 4, 5, 6, etc.) of the nucleic acid constructs of this invention; and b) regenerating the transgenic plant from the transformed plant cell, wherein the plant has increased resistance to infection and/or disease as compared with a plant that is not transformed with said nucleic acid construct.

Additional embodiments of this invention comprise a method of producing GmCPI1 in a plant, transforming a cell of the plant with one or more nucleic acid constructs of this invention encoding GmCPI1; b) regenerating the transgenic plant from the transformed plant cell; and c) collecting the GmCPI1 from the plant.

Use of plants as platforms for producing commercially valuable heterologous proteins is well-known in the art. See, for example, U.S. Pat. No. 6,040,498; U.S. Patent Application Publication No. 2009/0220543; WO2000/77174; U.S. Pat. No. 7,491,509 and *Plants as Factories for Protein Production*, eds. E. E. Hood and J. A. Howard, Kluwer Academic Publishers Norwell, Mass., pp 209 (2002). *Molecular farming: plant-made pharmaceuticals and technical proteins*, eds. R. Fischer and S. Schillberg; Wiley-VCH Verlag GmbH & Co. CGaA, Wienheim (2004).

The process of producing heterologous proteins from plants requires an initial choice of a plant system in which to express the heterologous protein(s) of interest. Many plants have been shown to be amenable to transformation via a wide variety of techniques. Non-limiting examples of transformable plants include tobacco, corn, *Arabidopsis*, soybean, cotton, carrot, asparagus, rice, turfgrass, lettuce, spinach, white clover, alfalfa, peanut, sunflower, canola, duckweed, wheat, cassava, sugar cane and the like. Expression of heterologous proteins in plants can be accomplished either by integrating the gene of interest into a plant genome, to create a transgenic plant that stably expresses the desired protein, or by introducing the nucleotide sequence of interest into a plant vector that can be introduced into, and transiently maintained in, plant cells. Once the plant is transformed and the production of the heterologous protein(s) is at a sufficient level, the plants can be harvested and the protein(s) collected and purified. Methods for collection and purification of proteins from plants are known in the art (See, e.g., WO2000/77174; U.S. Pat. No. 5,981,835; U.S. Pat. No. 6,846,968 and U.S. Application Publication No. 2005/0015830)

The term "transformation" as used herein refers to the introduction of a heterologous nucleic acid into a cell. Transformation of a cell may be stable or transient. The term "transient transformation" or "transiently transformed" refers to the introduction of one or more heterologous nucleic acids into a cell wherein the heterologous nucleic acid is not heritable from one generation to another.

"Stable transformation" or "stably transformed" refers to the integration of the heterologous nucleic acid into the genome of the plant or incorporation of the heterologous nucleic acid into the cell or cells of the plant (e.g., via a plasmid) such that the heterologous nucleic acid is heritable across repeated generations. Thus, in one embodiment of the present invention a stably transformed plant is produced.

Transient transformation may be detected by, for example, an enzyme-linked immunosorbent assay (ELISA) or Western blot, which can detect the presence of a peptide or polypeptide encoded by one or more transgene introduced into a plant. Stable transformation of a cell can be detected by, for example, a Southern blot hybridization assay of genomic DNA of the cell with nucleic acid sequences which specifically hybridize with a nucleotide sequence of a transgene introduced into a plant. Stable transformation of a cell can be detected by, for example, a Northern blot hybridization assay of RNA of the cell with nucleic acid sequences which specifically hybridize with a nucleotide sequence of a transgene introduced into a plant. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

A nucleotide sequence of this invention can be introduced into a plant cell by any method known to those of skill in the art. Procedures for transforming a wide variety of plant species are well known and routine in the art and described throughout the literature. Such methods include, but are not limited to, transformation via bacterial-mediated nucleic acid delivery (e.g., via *Agrobacteria*), viral-mediated nucleic acid delivery, silicon carbide or nucleic acid whisker-mediated nucleic acid delivery, liposome mediated nucleic acid delivery, microinjection, microparticle bombardment, electroporation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

Bacterial mediated nucleic acid delivery includes but is not limited to DNA delivery by *Agrobacterium* spp. and is described, for example, in Horsch et al. (*Science* 227:1229 (1985); Ishida et al. (*Nature Biotechnol.* 14:745 750 (1996); and Fraley et al. (*Proc. Natl. Acad. Sci.* 80: 4803 (1983)). Transformation by various other bacterial species is described, for example, in Broothaerts et al. (*Nature* 433: 629-633 (2005)).

Physical delivery of nucleotide sequences via microparticle bombardment is also well known and is described, for example, in Sanford et al. (*Methods in Enzymology* 217: 483-509 (1993)) and McCabe et al. (*Plant Cell Tiss. Org. Cult.* 33:227-236 (1993)).

Another method for physical delivery of nucleic acid to plants is sonication of target cells. This method is described, for example, in Zhang et al. (*Bio/Technology* 9:996 (1991)). Nanoparticle-mediated transformation is another method for delivery of nucleic acids into plant cells (Radu et al., *J. Am. Chem. Soc.* 126: 13216-13217 (2004); Torney, et al. *Society for In Vitro Biology*, Minneapolis, Minn. (2006)). Alternatively, liposome or spheroplast fusion can be used to introduce nucleotide sequences into plants. Examples of the use of liposome or spheroplast fusion are provided, for example, in Deshayes et al. (*EMBO J.*, 4:2731 (1985), and Christou et al. (*Proc Natl. Acad Sci. U.S.A.* 84:3962 (1987)). Direct uptake of nucleic acid into protoplasts using $CaCl_2$ precipitation, polyvinyl alcohol or poly-L-ornithine is described, for example, in Hain et al. (*Mol. Gen. Genet.* 199:161 (1985)) and Draper et al. (*Plant Cell Physiol.* 23:451 (1982)), Electroporation of protoplasts and whole cells and tissues is described, for example, in Donn et al, (In *Abstracts of VIIth International Congress on Plant Cell and Tissue Culture IAPTC*, A2-38, p 53 (1990); D'Halluin et al. (*Plant Cell* 4:1495-1505 (1992)); Spencer et al. (*Plant Mol. Biol.* 24:51-61 (1994)) and Fromm et al. (*Proc. Natl. Acad. Sci.* 82: 5824 (1985)). Polyethylene glycol (PEG) precipitation is described, for example, in Paszkowski et al. (*EMBO J.* 3:2717 2722 (1984)). Microinjection of plant cell protoplasts or embryogenic callus is described, for example, in Crossway (*Mol. Gen. Genetics* 202:179-185 (1985)). Silicon carbide whisker methodology is described, for example, in Dunwell et al. (*Methods Mol. Biol.* 111:375-382 (1999)); Frame et al. (*Plant J.* 6:941-948 (1994)); and Kaeppler et al. (*Plant Cell Rep.* 9:415-418 (1990)).

In addition to these various methods of introducing nucleotide sequences into plant cells, expression vectors and in vitro culture methods for plant cell or tissue transformation and regeneration of plants are also well known in the art and are available for carrying out the methods of this invention. See, for example, Gruber et al, ("Vectors for Plant Transformation" in *Methods in Plant Molecular Biology and Biotechnology*, Glick, B. R. and Thompson, J. E., Eds. (CRC Press, Inc., Boca Raton, (1993), pages 89-119).

The term "vector" refers to a composition for transferring, delivering or introducing a nucleic acid (or nucleic acids) into a cell. A vector comprises a nucleic acid comprising the nucleotide sequence to be transferred, delivered or introduced. In some embodiments, a vector of this invention can be a viral vector, which can comprise, e.g., a viral capsid and/or other materials for facilitating entry of the nucleic acid into a cell and/or replication of the nucleic acid of the vector in the cell (e.g., reverse transcriptase or other enzymes which are packaged within the capsid, or as part of the capsid). The viral vector can be an infectious virus particle that delivers nucleic acid into a cell following infection of the cell by the virus particle.

A plant cell of this invention can be transformed by any method known in the art and as described herein and intact plants can be regenerated from these transformed cells using any of a variety of known techniques. Plant regeneration from plant cells, plant tissue culture and/or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)). Methods of selecting for transformed transgenic plants, plant cells and/or plant tissue culture are routine in the art and can be employed in the methods of the invention provided herein.

A large variety of plants have been shown to be capable of regeneration from transformed individual cells to obtain transgenic plants. Those of skill in the art can optimize the particular conditions for transformation, selection and regeneration according to these art known methods. Factors that affect the efficiency of transformation include the species of plant, the tissue infected, composition of the medium for tissue culture, selectable marker coding sequences, the length of any of the steps of the methods described herein, the kinds of vectors, and/or light/dark conditions. Therefore, these and other factors can be varied to determine the optimal transformation protocol for any particular plant species. It is recognized that not every species will react in the same manner to the transformation conditions and may require a slightly different modification of the protocols disclosed herein. However, by altering each of the variables according to methods routine in the art, an optimum protocol can be derived for any plant species.

Accordingly, in one embodiment, a heterologous nucleotide sequence is introduced into a cell of a plant of the present invention by co-cultivation of the cell with *Agrobacterium tumefaciens* to produce a transgenic plant. In a further embodiment, a heterologous nucleotide sequence is introduced into a cell of a plant of the present invention by direct nucleic acid transfer to produce a transgenic plant.

```
                                  SEQUENCES
  Amino acid sequence of soybean cysteine protease inhibitor having GenBank ®
  Database Accession No. XP_003524913 and GenBank ® Database Accession No.
  XP_003524914 (SEQ ID NO: 1):
              1 maalirspav ilailtisac iactasyggl vggrskipdv kankkvqdlg rfsveehnrm 61 lrqaqkeeeq vtfvevveaq qqvvsgikyy mkisatqggd ggdsrifesv vvvkpwlrsk 121 qllnfapstq Nucleotide sequence for amino acid sequence of GenBank ® Database Accession
  No. XP_003524913 has GenBank ® Database Accession No. XM_003524865 (SEQ ID
  NO: 2):
              1 atcgttctaa attaattcta acaggttcgg cataattgag cgatcgatgg cggcgttgat 61 aaggtcaccg gcggtgatac tggcgatcct gacgatctcg gcgtgcatcg cgtgtacggc 121 gtcgtacggg ggattggtcg ggggaaggtc gaagatccct gacgtgaagg cgaacaagaa 181 ggtgcaggat ctagggcggt tctcggtgga ggagcataac cggatgctga ggcaggcgca 241 gaaggaggag gagcaagtca cgttcgtgga agtggtggag gcgcaacaac aagtggtgtc 301 tgggatcaag tactacatga agatatcggc cacgcagggt ggcgacggtg gagattccag 361 aatattcgaa tccgttgtgg tggtgaagcc gtggcttcgt tccaagcagc ttctcaattt 421 cgctccttcc acgcagtgaa atacgatcaa tttcggttcc gtttcaatta ctttttttaac 481 tcataataac atgcttaatt ggtttagtat gctttaatcc ttctaataaa aaatatgaaa 541 gagagaaata aatgtttaca atttctgttt cagacatgaa tcaactggtt aacaggttaa 601 caataatgtc aaagatatat ttacattgtt ttgagcatgg a
  //
  Nucleotide sequence for amino acid sequence of GenBank ® Database Accession
  No. XP_003524914 has GenBank ® Database Accession No. XM_003524866) (SEQ ID
  NO: 4):
              1 atcgttctaa attaattcta acaggttcgg cataattgag cgatcgatgg cggcgttgat 61 aaggtcaccg gcggtgatac tggcgatcct gacgatctcg gcgtgcatcg cgtgtacggc 121 gtcgtacggg ggattggtcg ggggaaggtc gaagatccct gacgtgaagg cgaacaagaa 181 ggtgcaggat ctagggcggt tctcggtgga ggagcataac cggatgctga ggcaggcgca 241 gaaggaggag gagcaagtca cgttcgtgga agtggtggag gcgcaacaac aagtggtgtc 301 tgggatcaag tactacatga agatatcggc cacgcagggt ggcgacggtg gagattccag 361 aatattcgaa tccgttgtgg tggtgaagcc gtggcttcgt tccaagcagc ttctcaattt 421 cgctccttcc acgcagtgaa atacgatcaa tttcggttcc gtttcaatta ctttttttaac 481 tcataataac atgcttaatt ggtttagtat gctttaatcc ttctaataaa aaatatgaaa
```

| SEQUENCES |
| --- |

```
       541 gagagaaata aatgtttaca atttctgttt cagacatgaa tcaactggtt aacaggttga 601 attgtac
```

Amino acid sequence of soybean cysteine protease inhibitor from PI437654 (SEQ ID NO: 3)

```
         1 maalirspav ilailtisac iactasyggl vggrskipdv kankevqdlg rfsveehnrm 61 lrqaqkeeeq vtfvevveaq qqvvsgikyy mkisatqggd ggdsrifesv vvvkpwlrsk 121 qllnfapstq
```

GmCPI cDNA sequences of soybean variety PI437654 (for plant transformation) (SEQ ID NO: 5)

ATGGCGGCGTTGATAAGGTCACCGGCGGTGATACTGGCGATCCTGACGATCTCGGCGTGCATCGCGTGTACGGCG

TCGTACGGGGGATTGGTCGGGGGAAGGTCGAAGATCCCTGACGTGAAGGCGAACAAGGAGGTGCAGGATCTAGGG

CGGTTCTCGGTGGAGGAGCATAACCGGATGCTGAGGCAGGCGCAGAAGGAGGAGGAGCAAGTCACGTTCGTGGAA

GTGGTGGAGGCGCAACAACAAGTGGTGTCTGGGATCAAGTACTACATGAAGATATCGGCCACGCAGGGTGGCGAC

GGTGGAGATTCCAGAATATTCGAATCCGTTGTGGTGGTGAAGCCGTGGCTTCGTTCCAAGCAGCTTCTCAATTTC

GCTCCTTCCACTCAGTGA

GmCPI genomic DNA sequences of soybean variety PI437654 (for plant transformation), Size: 5890 by (SEQ ID NO: 6)

ACTAATTCTTGAGGAAAGACAGGAAGAAATAGATAAAAAGAAAAAGAAAAAAGGAAGAAGAGGAAGAAATCAACT

GCAGTATAAAGTCCAGAACCCAATACATAATAATATAATTTTAAAACAAGATAAATAATAATAAAATAATTACAG

CATGATGGTAGACGCGTGGTGGCCAACAACGGTTCCATGGCCAAATCGAAGGCTCGTGCAGCCATGGGCCCATCA

CGAGAAACCTGGACCGGAAGAGGGCGGAACGGAGTGGAGTGGGTGGGAAAGGAAAAAGAGGGGTAAAAAAAGAAG

AAAGAAGAGAAATTATATAGATAAATAAATAATTTAAGTAAGAATAAATTTTGTATTTCCGTTTCAAAATAAAAA

ATATATATATAATTAATCATTTTAAAATAAATATTAGAAGGTAAGTCTTTTGTGAGATTTAAAAAAAGATTTTAG

ATCTAAAAATGAGATTTGCTATTAGATTAAAAAATTTAAAAAGTATGATACGGATAAATTTATCAAAAAAATTAT

TAAGATCTCAAAAATAAAATCTATTATGAGAGGAGTTCTTGGAAGCATACAGTATCCTCCAAAAAAAGAAAAGAA

GGGATGAACAGTTTATTAGTTTCAAGTTTTCCATTTTGAGTCAAGTGTTAATCTACATAGAATTTGAGTAAACAA

TTTAATAACACGTAGCCTCCGAAACATAATAAATTTGGCCGTTTAGAAAAGCAATAAACAAGTTCTCGAGGGATT

TCTAGCAACGATGCCGTTGTGCTCAAATTCTTGTCGAATTTTTTCTATGATCGATCTTCCACCATGAGATTTGAC

TTTCCTCACATTTTCAAGTTTCTGCAATGCATTCTTTCTTCAACCTCATAACCCGTTCCTTCAAAACTGCTTTTG

GAAGTAGTGGCTACCTTATTCCGATGAGCTTCGAGGACTGCCTTCTCATCATTTATAGCAAAGGCTTGTTTGATG

GAATATAGAATGCTTGGGAACTCTTTGCGCTTAGAGTATATCATATCTTTAAGTTCATATGTACATCTGTGAATA

ATCTGTCTTACCTTTGAATATCGGGCGATAAGGATAAATAGGAGTCAACAACTTGTTTGCAATGAGGCTCTATAA

TGACGTTTTGCATATTCAATTCATTCTACTTTTGGTCCCAGTAATTTTAAAATCAATCAATTTGATCTTATAAGT

TTAAAAATAGATAAATTTAATCCTTAGGCTTCGATTGTTGAGAAACTAAAAATAGACTAAATTTATCTTCTTTTT

TTTAACATAAAGATCAAACTGATCGGTTTAAAATTACAGCGACTAAAATTAAATTTTGTTCAATCTTTAAAAACC

TATTTTAGCCTTAAATCTTGTGATCCATAACTATATATTAATACATTTTATTGCATGATTTTTACTTCTTCTTTT

TATCTCCACGAGATATAAACATTTACCAAATGTAGTCATTTATGTTCATACACTTTCACATAAACAGTTGTCTTT

GTGATACATTCTACATAAAACTTGTGTACCAAGAAAGAAGAAAATACATCTTTGTAATAAAAGCAACTGAGGTAG

TTTTAATTATGGTAGTAATTGCCTTTTGTCATTCTTCCTCAGCAGTCATCCCCATGGCTCAGGAATATGGGCTC

GTGTACCCCCCTTGGAATTGGGCTGAGTATTCGTTGAACATAGCCACGTCTCTATAGCCTTTTTCAGTCAGAATT

AACAATCGTCATAATAAATTAATCATGAGTAGTATTAATAATTAGGCTAGAATTACCAGTTACAAGTAGCAAAAA

CTACAAATATTACTCCTTTTTTCACCTGGTTTATCTCTTTCGTATTAAATTTCACCTAATTTATTTCTTTCGTAT

-continued

SEQUENCES

TAATATGACCTTTATTATAAAGCAATCATTCATCACAAGAGTGAGGCAGAATACAAATGGCATACAAAATTTTAC

TTTTATATTTGATAGTTTATAGCTCAACCATTTGATGAAACACAAAAGATACGAGAAGAGACACGAAAAATACCA

CCACAAAAAGCTTGAGCGGAGTCTATATATACACGAAGAAAGTCATCTACTTATTCTATTATAATAATTATTAAT

TATTTATTCTATCTCATAATTATTTTTAAAATTTGTACCCTCCTAATCGTCGATCCACACTTAGATGAGTGCCAA

TTGACCTCATTAGGACAGCAAAAATTAACACTTTAATCTTATCTCAAAGTCATATTTACGGCACCATACGAGATA

TAATGTGGAATTGAACCCAAAGGAATGTAGGTTACAAATATACACTTAGATGCTCTAACTACTGGTTCTTTCAAT

TCTAGTTCTAGGAACGATTTATATTGGAATAAAATTAAACATGAAATAAGTGTTATGCATTACTAATATTTATCT

AGCTCTCAACAACAAATCTAATGCATTAAAGTGTAACTGAACCAAACACCATCTTAAAAACAATAGAATTAAACT

GAAAAAAAAATTATAAATTAATCCGTGTATAGTGGCGGACAGTTATGCAAACTGCATGTAGTATACGTGGAAG

CCTCTGAGATTAGTGCTAGCCAATGTGTCAGTTTGTGGTAACCACACCAAGCCAACTCGATCGTGACTAGACCCG

TTTACGGCAACAACCTTAAACAAACAAAATGAAAAAGCAATCTCGTTTGCATCCAAAACTCGCGTCCCAATCGC

GACACGCACGCGGTTTTCGTTTCCCCACCATTCACCGTCTCTCGGTTAGTTTTTCATGCGTATCCAAACACCTCT

TTCCCCCTTTATATAAACGACACCGTATACGCAACTCCATCATCGTTCTAAATTAATTCTAACAGGTTCGGCATA

ATTGAGCGATCGATGGCGGCGTTGATAAGGTCACCGGCGGTGATACTGGCGATCCTGACGATCTCGGCGTGCATC

GCGTGTACGGCGTCGTACGGGGGATTGGTCGGGGGAAGGTCGAAGATCCCTGACGTGAAGGCGAACAAGGAGGTG

CAGGATCTAGGGCGGTTCTCGGTGGAGGAGCATAACCGGATGCTGAGGCAGGCGCAGAAGGAGGAGGAGCAAGTC

ACGTTCGTGGAAGTGGTGGAGGCGCAACAACAAGTGGTGTCTGGGATCAAGTACTACATGAAGATATCGGCCACG

CAGGGTGGCGACGGTGGAGATTCCAGAATATTCGAATCCGTTGTGGTGGTGAAGCCGTGGCTTCGTTCCAAGCAG

CTTCTCAATTTCGCTCCTTCCACTCAGTGAAATACGATCAATTTCGGTTCCGTTTCAACTACTTTTTTAACTCAT

AATAACATGCTTAATTGGTTTAGTATGCTTTAATCCTTCTAATAAAAAATATGAAAGAGAGAAATAAATGTTTAC

AATTTCTGTTTCAGACATGAATCAACTAGTGAACAGGTTAAATTGTCAAATATCTAAAGATATATTTACATTGTT

TTGAGCATGAGTCTCTCTATGTTTTTTTTAATCTACTATGGGCATATTTTATCTTAGAGGAGTGATACTTTGTAC

AGATATCATTTCTCTAACTTTTATTATCATTTATAAACGTTAAACGATATTATTATGAAGTTTGTCTCAATGAAT

TAAAATGTTTAGGTTATTAAGACTGGATAATCTAGGCGTGTATTCAATTACGACGTTTATTTCGTGGACATTTTT

TTTTGTCTCGGGAATTTATTTATTTTTTCCTCATAATATAGCATGACAATGTTATTTTTGGGTTCCTTATATATG

CTCTAAAAAAATTGTTTGGTTAATTATTAAAATTGACTGTAAATGTTTTTATATTCTCATAAATAAAACACGTG

TGCTTGATTGAGTTATTTTTTTGTTGAGAGTTTGATTGAGTTATTAATTTCTAACTTTGCATAAGTGATAAGTA

AGTTTTCTATCTAATAACATACACATAACACCTTTCAGTATGTAACTGAGTATCTTTCACGAATATATATATATA

TATATATATAGAGAGAGAGAGAGAGAGAGAGAGAGAGAGAGAGAGAGAGAGAGCAATTCCAATATGCCT

ATTTTGCGTGACAATGTTATTTATTTTTTTTTGTCTCGGGAATTTATTTATTTTTCCTCATAATATAGCATGA

CAATGTTATTTTTGGGTTCCTTATATATGCTCTAAAAAAATTGTTTGGTTAATTATTAAAATTGACTGTAAATGT

TTTTTATATTCTCATAAATAAAACACGTGTGCTTGATTGAGTTATTTTTTTGTTGAGAGTTTGATTGAGTTATT

AATTTCTAACTTTGCATAAGTGATAAGTAAGTTTTCTATCTAATAACATACACATAACACCTTTCAGTATGTAAC

TGAGTATCTTTCACGAATATATATATATATATATATAGAGAGAGAGAGAGAGAGAGAGAGAGAGAGAGAGAGA

GAGAGAGAGAGAGAGAGAGAGAGAGAGAGAGAGAGAGAGAGAGAGAGAGAGAGAGAGAGAGAGAGAGCAAT

TCCAATATGCCTATTTTGCGTGAATGAAATTGGCACATAGGGATGAAAATTGTGGCAAAGAAAAAAACTATATT

ATGTAACATGAAGGAGGAGCATTGAGAGGGTAGTACGGAGAATATGTTTGGATTTTTATTCATAAAGAGATTTCT

GTCACGAGAATAAATTTTCATAGTTTTACGTTCAATAATAAACAGAATAACTTTTATAGTTATAATAATGGTAGT

SEQUENCES

```
ATTAGGAATTATTTTAGCTATTTCTCAACAAAATATTAAGAAAATTTTGGTCTATTACACGATGTCTCGATTGAA

TTATATGATCTAGGTATGGGATATTATGGAGTCCGAGATTAAATATTAATCCTACGTAAATTATAACTTACATAG

AAATAAAATATGTTTAAAATTAATTATTTTATTACTTCATAATAAATATGGGATAAAAATTTCTACCTGTATTCG

TGGGATTACAAAAATTAATTGAGTAAGACCGCTTCTCCATCTGTCATTATTGAATTGTTGAGAAGATATATACAA

AATATTTTGGTGAAAAATTACAGGGAATAAAAAAATTGTATAAGGTATAATACTTTTAATGAAAGATATAAGAAG

ATATTTATTGTTATTATTTAGTCATTGAGTAAATTTTTTTTAAGAAATATATAAGGACGTCTTACAATAGTGC

AAATAGCATTTCACATTTGAGTATAAAAAGTATTTCGTCAACTTTTTCTCTTCTTTAAATCAAATCGTCCTCTAG

CCATACTTTTTTTATCTAAAAAAGTTTAAGATAAATATGAAGAGATCTACACCAACTTATTAATTATATTTTTAT

TTTATTTAAAAAGTTAAAAAAAAAACTACAGAGAGACTTGCCTCTTATTTTCTTCCAATATAGAAATAAGAATAA

TAAACACTCAAAAGAAAAAAATATTAGAAAAAAAATAAGAATTATTTCAGGTAAATATAATTTTGATGTCTGAAA

ATGTGAAATGATAACAAATTGGTCGCTAGAAAAACTCAAATTTAGTTTTTCAAATATAAAAAAATATAATTGATT

AGTCATATACACAATTTAATGACAAATTAATACATAAATTTTATAGTTTAATGTTAAATTAATTTTTAAAAATAT

AATTTATTTTTAAATTATTTTTTAAATATTATAACTTAATTACAAAATAATTTCATAAATTTAACAATAATAATA

TATTACAGTTTTTACACATTCATTGTATTTAAATTTTTTATCTTTAAACAACCAATAATTTATTTATTTTTTCT

AAGAAAAACGACAAGCTCAATATAGAAACTAGAAAGTAAATTTATTTTATCAGGTACACACAAGAACCGTACACG

CGCTGACATTCAAATCCCTCCCATTTCCCAACTCCCAACT
```

>Access information of CPI in Soybean variety Williams 82
Glyma05g28250 Details
Name: Glyma05g28250
Type: gene
Description:
Source:     Glyma1
Position:   Gm05:34114859..34115544 (- strand)
Length:     686
load_id:    Glyma05g28250
Parts: Type: mRNA
Description:
Source:     Glyma1
Position:   Gm05:34114859..34115544 (- strand)
Length:     686
load_id:    Glyma05g28250.1
parent_id:  Glyma05g28250
Parts: Type: five_prime_UTR
Description:
Source:     Glyma1
Position:   Gm05:34114859..34115105 (- strand)
Length:     247
parent_id:  Glyma05g28250.1
Type: CDS
Description:
Source:     Glyma1
Position:   Gm05:34115106..34115498 (- strand)
Length:     393
parent_id:  Glyma05g28250.1
Type: five_prime_UTR
Description:
Source:     Glyma1
Position:   Gm05:34115499..34115544 (- strand)
Length:     46
parent_id:  Glyma05g28250.1
 Glyma05g28250 (from Williams 82) (SEQ ID NO: 7)

```
ATCGTTCTAAATTAATTCTAACAGGTTCGGCATAATTGAGCGATCGATGGCGGCGTTGATAAGGTCACCGGCGGT

GATACTGGCGATCCTGACGATCTCGGCGTGCATCGCGTGTACGGCGTCGTACGGGGGATTGGTCGGGGGAAGGTC

GAAGATCCCTGACGTGAAGGCGAACAAGAAGGTGCAGGATCTAGGGCGGTTCTCGGTGGAGGAGCATAACCGGAT

GCTGAGGCAGGCGCAGAAGGAGGAGGAGCAAGTCACGTTCGTGGAAGTGGTGGAGGCGCAACAACAAGTGGTGTC

TGGGATCAAGTACTACATGAAGATATCGGCCACGCAGGGTGGCGACGGTGGAGATTCCAGAATATTCGAATCCGT
```

| SEQUENCES |
|---|
| TGTGGTGGTGAAGCCGTGGCTTCGTTCCAAGCAGCTTCTCAATTTCGCTCCTTCCACGCAGTGAAATACGATCAA |
| TTTCGGTTCCGTTTCAATTACTTTTTTAACTCATAATAACATGCTTAATTGGTTTAGTATGCTTTAATCCTTCTA |
| ATAAAAAATATGAAAGAGAGAAATAAATGTTTACAATTTCTGTTTCAGACATGAATCAACTGGTTAACAGGTTAA |
| CAATAATGTCAAAGATATATTTACATTGTTTTGAGCATGGAGTCTCTCTATGTTTTTTTTTTAATCTACTATGG |
| GCATATTTTAT |
| GmCPI Genomic DNA (Williams 82) Sequence position = Gm05:34112722..34118373 (- strand). Size: 5,652 by (SEQ ID NO: 8) TTGTATCTCTTCCTAACTAATTCTTGAGGAAAGACAGGAAGAAAAAGAAAAAAGGAAGAAGAGGAAGAAATCAAC |
| TGCAGTATAAAGTCCAGAACCGAATACATAATAATATAATTTTAAAACAAGATAAATAATAATAAAATAATTACA |
| GCATGATGGTAGACGCGTGGTGGCCAACAACGGTTCCATGGCCAAATCGAAGGCTCGTGCAGCCATGGGCCCATC |
| ACGAGAAACCTGGACCGGAAGAGGGCGGAACGGAGTGGAGTGGGTGGGAAAGGAAAAAGAGGGGTAAAGAAAGAA |
| GAAAGAAGAGAAATTATATAGATAAATAAATAATTTAAGTAAGAATAGATTTTGTATTTCCGTTTCAAAATAAAA |
| AATATATATATAATTAATCATTTTAAAATAAATTATAAATAAATATTAGAAGGTAAGTCTTTTGTGAGATTTAAA |
| AAAGATTTTAGATCTAAAAATGAGATTTGCTATTAGATTAAAAAATTTAAAAAGTATGATACGGATAAATTTAT |
| CAAAAAATTTATTAAGATCTCAAAAATAAAATCTGTTATGAGAGGAGTTCTTGGAAGCATACAGTATCCTCCAAA |
| AAAAGAAAGAAGGGATGAACAGTATATTAGTTTCAAGTTTTCCATTTTGAGTCAAGTGTTAATCTACATAGAAT |
| TTGAGTAAACAATTTAATAACACATAGCCTCCGAAACATAATAAATTTGGCCGTTTAGAAAAGCAATAAACAAGT |
| TCTCGAGGGATTTCTAGCAACGATGCCGTTGTGCTCAAATTCTTGTCGAATTTTTTCTATGATCGATCTTCCACC |
| ATGAGATTTGACTTTCCTCACATTTTCAAGTTTCTGCAATGCATTCTTTCTTCAACCTCATAACCCGTTCCTTCA |
| AAACTGCTTTTGGAAGTAGTGGCTACCTTATTCCGATGAGCTTCGAGGACTGCCTTCTCATCATTTATAGCAAAG |
| GCTTGTTTGATGGAATATAGAATGCTTGGGAACTCTTTGCGCTTAGAGTATATCATATCTTTAAGTTCATATGTA |
| CATCTGTGAATAATCTGTCTTACCTTTGAATATCGGGCGATAAGGATAAATAGGAGTCAACAACTTGTTTGCAAT |
| GAGGCTCTATAATGACGTTTTGCATATTCAATTCATTCTACTTTTGGTCCCAGTAATTTTAAAATCAATCAATTT |
| GATCTTATAAGTTTAAAAATAGATAAATTTAATCCTTAGGCTTCGATTGTTGAGAAACTAAAAATAGACTAAATT |
| TATCTTCTTTTTTTTAACATAAAGATCAAACTGATCGGTTTAAAATTACAGCGACTAAAATTAAATTTTGTTCA |
| ATCTTTGAAAACCTATTTTAGCCTTAATTCTTGTGATCCATAACTATATATTAATACATTTTATTGCATGATTTT |
| TACTTCTTCTTTTTATCTCCACGAGATATAAACATTTACCAAATGTAGTCATTTATGTTCATACACTTTCACATA |
| AACAGTTGTCTTTGTGATACATTCTACATAAAACTTGTGTACCAAGAAGAAGAAAATACATCTTTGTAATAAAA |
| GCAACTGAGGTAGTTTTAATTATGGTAGTAATTGCCTTTTGTCATTCTTCCTCAGCAGTCATCCCCATGGCTCAG |
| GAATATGGGGCTCGTGTACCCCCCTTGGAATTGGGCTGAGTATTCGTTGAACATAGCCACGTCTCTATAGCCTTT |
| TTCAGTCAGAATTAACAATCGTCATAATAAATTAATCATGAGTAGTATTAATAATTAGGCTAGAATTACCAGTTA |
| CAAGTAGCAAAAACTACAAATATTACTCCTTTTTTCACCTGGTTTATCTCTTTCGTATTAAATTTCACCTAATTT |
| ATTTCTTTCGTATTAATATGACCTTTATTATAAAGCAATCATTCATCACAAGAGTGAGGCAGAATACAAATGGCA |
| TACAAAATTTTACTTTTATATTTGATAGTTTATAGCTCAACCATTTGATGAAACACAAAAGATACGAGAAGAGAC |
| ACGAAAAATACCACCACAAAAAGCTTGAGCGGAGTCTATATATACACGAAGAAAGTCATCTACTTATTCTATTAT |
| AATAATTATTAATTATTTATTCTATCTCATAATTATTTTTAAAATTTGTACCCTCCTAATCGTCGATCCACACTT |
| AGATGAGTGCCAATTGACCTCATTAGGACAGCAAAAATTAACACTTTAATCTTATCTCAAAGTCATATTTACGGC |
| ACCATACGAGATATAATGTGGAATTGAACCCAAAGGAATGTAGGTTACAAATATACACTTAGATGCTCTAACTAC |
| TGGTTCTTTCAATTCTAGTTCCAGGAACGATTTATATTGGAATAAAATTAAACATGAAATAAGTGTTATGCATTA |
| CTAATATTTATCTAGCTCTCAACAACAAATCTAATGCATTAAAGTGTAACTGAAGCAAACACCATCTTAAAAACA |

-continued

SEQUENCES

ATAGAATTAAACTGAAAAAAAAAATTATAAATTAATCCGTGTATAGTGGCGGGACAGTTATGCAAACTGCATGTA

GTATACGTGGAAGCCTCTGAGATTAGTGCTAGCCAATGTGTCAGTTTGTGGTAACCACACCAAGCCAACTCGATC

GTGACTAGACCCGTTTACGGCAACAACCTTAAACAAACAAAAATGAAAAAGCAATCTCGTTTGCATCCAAAACTC

GCGTCCCAATCGCGACACGCACGCGGTTTTCGTTTCCCCACCATTCACCGTCTCTCGGTTAGTTTTTCATGCGTA

TCCAAACACCTCTTTCCCCCTTTATATAAACGACACCGTATACGCAACTCCATCATCGTTCTAAATTAATTCTAA

CAGGTTCGGCATAATTGAGCGATCGATGGCGGCGTTGATAAGGTCACCGGCGGTGATACTGGCGATCCTGACGAT

CTCGGCGTGCATCGCGTGTACGGCGTCGTACGGGGATTGGTCGGGGAAGGTCGAAGATCCCTGACGTGAAGGC

GAACAAGAAGGTGCAGGATCTAGGGCGGTTCTCGGTGGAGGAGCATAACCGGATGCTGAGGCAGGCGCAGAAGGA

GGAGGAGCAAGTCACGTTCGTGGAAGTGGTGGAGGCGCAACAACAAGTGGTGTCTGGGATCAAGTACTACATGAA

GATATCGGCCACGCAGGGTGGCGACGGTGGAGATTCCAGAATATTCGAATCCGTTGTGGTGGTGAAGCCGTGGCT

TCGTTCCAAGCAGCTTCTCAATTTCGCTCCTTCCACGCAGTGAAATACGATCAATTTCGGTTCCGTTTCAATTAC

TTTTTTAACTCATAATAACATGCTTAATTGGTTTAGTATGCTTTAATCCTTCTAATAAAAATATGAAAGAGAGA

AATAAATGTTTACAATTTCTGTTTCAGACATGAATCAACTGGTTAACAGGTTAACAATAATGTCAAAGATATATT

TACATTGTTTTGAGCATGGAGTCTCTCTATGTTTTTTTTTTAATCTACTATGGGCATATTTTATCTTAGAGAAG

TGATACTTTGTACAAATATCATTTCTCTAACTTTTATTATCATTTATAAACGTTAAACGATATTATTATGAAGTT

TGTCTCAATAAATTAAAATGTTTAGGCGTTATTAAGACTGGATAATCTAGGCGTGTATTCAATTACGACGTTTAT

TTCGTGGACATTTTTTTGTCTCGGGAATTTATTTATTTTTTCCTCATAATATAGCATGACAATGTTATTTTTGG

GTTCCATATATATGCTCTAAAAAAATTGTTTGGTTAATTATTAAAATTGACTGTAAATGTTTTTATATTCTCAT

AAATAAAACACGTGTGCTTGATTGAGTTATTTTTTTGTTGAGAGTTTGATTGAGTTATTAATTTCTAACTTTGC

ATAAATGTTAAGTAAGTTTTCTATCTAATAACATACACATAACACCTTTCAGTATGTAACTGAGTATCTTTCACG

AATATATATATATATATATATATATATATATATAGAGAGAGAGAGAGAGAGAGAGAGAGAGAGAGAAGAGAGA

GAGAGAGAGAGAGAGAGAGAGCAATTCCAATATGCCTATTTTGCGTGAATGAAATTGGCACATAGGGATGAAA

ATTATGGCAAAGAAAAAAAACTATATTATGTAACATAAAGGAGCATTGAGAGGGTAGTAAGGAGAATATGTTTGG

ATTTTTATGAATGTTGCGTGAATGAAATTGGCACATAAGAACTAAATTGGTGGAAAGAAACTGTCACGAGAATAA

ATTTTCATAGTTTTACGTTCAATAATAAACAGAATAACTTTTATAGTTATAATAATGGTAGTATTAGGAATTATT

TTAGCTATTTCTCAACAAAATATTAAGAAAATTTTGGTCTATTACACGATGTCTCGATTGAATTATATGATCTAG

GTATGGGATGTTATGGAGTCCGAGATTAAATATTAATCCTACGTAAATTATAACTTACATAGAAATAAAATATGT

TTAAAATTAATTATTTTATTACTTCATAATAAATATGGGATAAAAATTTCTACCTGTATTCGTGGGATTACAAAA

ATTAATTGAGTAAGACCGCTTCTCCATCTGTCATTATTGAATTGTTGAGAAGATATATACAAAATATTTTGGTAA

AAAATTACAGGGAATAAAAAAATTGTATAAGGTATAATACTTTTAATGAAAGATATAAGAAGATATTTTATTGTT

ATTATTTAGTCATTGAGTAAATTTTTTTTAAGAAATATATAAGGACCTCTTACAATAGTGCAAATAGCATTTCA

CATTTGAGTATAGAAAGTATTTCGTCAACTTTTTCTCTTCTTTAAATCAAATCGTCCTCTAGCCATACTTTTTTT

ATCTAAAAAAGTTTAAGATAAATATGAAGAGATCTACACCAACTTATTAATTATATTTTATTTTATTTAAAAAG

TTAAAAAAAAACTACAGAGAGACTTGCCTCTTATTTTCTTCCAATATAGAAATAAGAATAATAAACACTCAAAAG

AAAAAAATATTAGGAAAAAAATATTAGAAAAAAATAAGAATTATTTCAGGTAAATATAATTTTGATGTCTGAAAA

TGTGAAATGATAACAAATAATCGGATTTCGAAATCAAATAACGCCTCATCTATAAAAATGGAAATATTTTGAAAA

AAAAAACGTTTTTTTTTCAAAATATTTCAAAAGGTACACAAATAAATAAGACAATTCTGAAGCTTTTTGTGCA

ATTTAATTTCTAATTAAGTTCAATTCTCATCAGTAAAAAAGTGGTACACCCAAAAATACAGATAATTCGCCAGCT

-continued

SEQUENCES

```
TTATGTGCAATTTGTGTCCCATTCAAATTATCTTCAATAGGAGTCAAGGGAAGAACTCAAATTTAGTTTTTTAAA
TATAAAAAAATATAATTGATTAGTCATATACACAATTTAATTTAATGACAAATTAATACATAAATTTTTTTACAC
ATTCATTGTATTTAAATTTTTTATCTTTAAACAACCAATAATTTATTTATTTATTTCTAAGAAAAACGACAAGCT
CAATATAGAAACTAGAAAGCTCAATAATTTATTTTATCAGGTACACACAAGAACCGTACACGCGCTGACATTCAA
ATCCCTCCCATTTCCCAACTCCCAACT
```

EXAMPLES

Example 1

GmCPI1, a Soybean Cysteine Protease Inhibitor is Involved in Plant Response to Biotic Stress Abstract A soybean cysteine protease inhibitor gene GmCPI1 was cloned from a nematode-resistant genotype. Transgenic *Arabidopsis* plants overexpressing GmCPI1 of PI437654 exhibited dramatically enhanced resistance against thrips. A transient assay using soybean root transformation demonstrated that compared to wild-type control plants, transgenic soybean roots overexpressing GmCPI1 of PI437654 had a 60% decrease in nematode infection. This demonstrates the great potential of using a similar strategy to improve other food plants and economically important crops for enhanced pest and disease resistance, enhancing agricultural production.

Introduction Protease activity is regulated by binding to specific cofactors and inhibitors. Protease inhibitors (PIs) represent a class of molecules that inhibit their target protease functions. Most PIs are proteins of small molecular size of approximate 12-16 kDa, without disulphide bridges and lack of putative glycosylation sites. Cysteine protease inhibitors (CPIs) inhibit function of cysteine proteases due to a tight and reversible interaction among them. It involves the N-terminal part of the protein, and two hairpin loops in which a conserved QxVxG motif and a Trp residue are located. N-terminal glycine in CPI is essential for binding to protease target. CPIs have a plant-specific signature ([LVI]-[AGT]-[RKE]-[FY]-[AS]-[VI]-x-[EDQV]-[HYFQ]-N) located in an α-helix.

Cysteine protease inhibitors occur mainly as single domain proteins. However some extracellular proteins such as kininogen, His-rich glycoprotein and fetuin also contain these domains (NCBI conserved domain CY). CPIs may provide an alternative to traditional therapy in drug-resistant organisms. In the present study, experiments were conducted to functionally characterize a soybean cysteine protease inhibitor gene (CPI1) from the nematode resistant variety PI437654, to reveal the role CPI1 plays in plant development and in responding to adverse environmental conditions, and explore their potential application for crop improvement and drug discovery using biotechnology approaches.

A genetic map of the CPI gene region in chromosome 5 was constructed based on the molecular marker (soybase.org) of F2 plants from the cross of Williams 82×PI437654. The BAC library of the soybean cyst nematode (SCN) resistant variety PI437654 was constructed and the corresponding BACs were screened and sequenced. A polymorphism was detected between Williams 82 and PI437654 (FIG. 1).

FIG. 1. Structural features and amino acid sequences of soybean Williams 82 and PI437654. The cysteine protease inhibitor protein contains a CY superfamily domain. A lysine in the deduced protein sequence of Williams 82 is substituted by a glutamic acid in the predicted protein sequence of variety PI437654. Table 1 shows the coding sequence that results in this amino acid residue difference between SCN resistant and susceptible cultivars.

Figure 7:
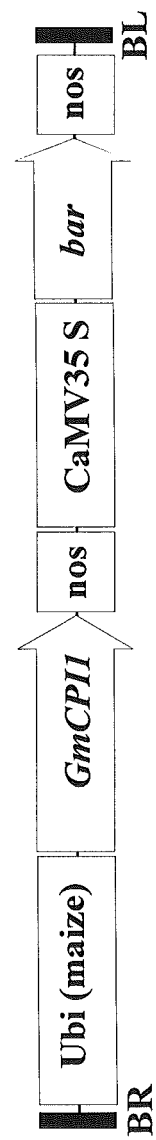
FIG. 7. A corn ubiquitin promoter driving the GmCPI1 cDNA of P1437654, linked to a CaMV 35S promoter-driven herbicide resistance gene, bar as selectable marker for plant transformation (e.g., pHKHL02).
Figure 8:
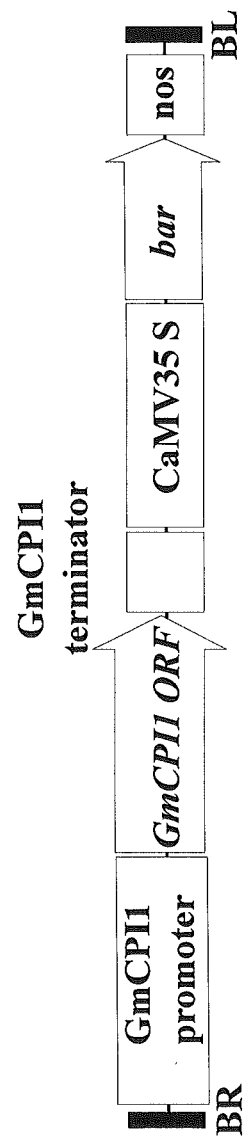
FIG. 8. The genomic sequence from PI437654 includes GmCPI1 5' regulatory region (promoter), GmCPI1 open reading frame (ORF), and GmCPI1 terminator. This DNA fragment is linked to a CaMV 35S promoter-driven herbicide resistance gene, bar as selectable marker for plant transformation (e.g., pHKHL01).

FIG. 2. A. Chimeric gene constructs for characterization of GmCPI gene. (See also FIGS. 7 and 8) B. CPI transcripts were detected in transgenic *Arabidopsis thaliana* plants harboring the PI437654 GmCPI1 gene (cDNA driven by a corn ubiquitin promoter; pHKHL02)), and a 6 kb genomic DNA fragment containing a 3.7 kb of the predicted promoter, the GmCPI1 ORF and a 1.9 kb of predicted GmCPI1 terminator (pHKHL01), respectively. C. Histochemical analysis of GmCPI1 promoter-driven GUS expression (PHL627) in transgenic *A. thaliana* $T_0$ plants. Flower at pollination stage; GUS expression is detected mainly in anthers and ovules, and less in sepals and petals. GUS staining is strong in pollen, but not in anther locules.

Figure 3:
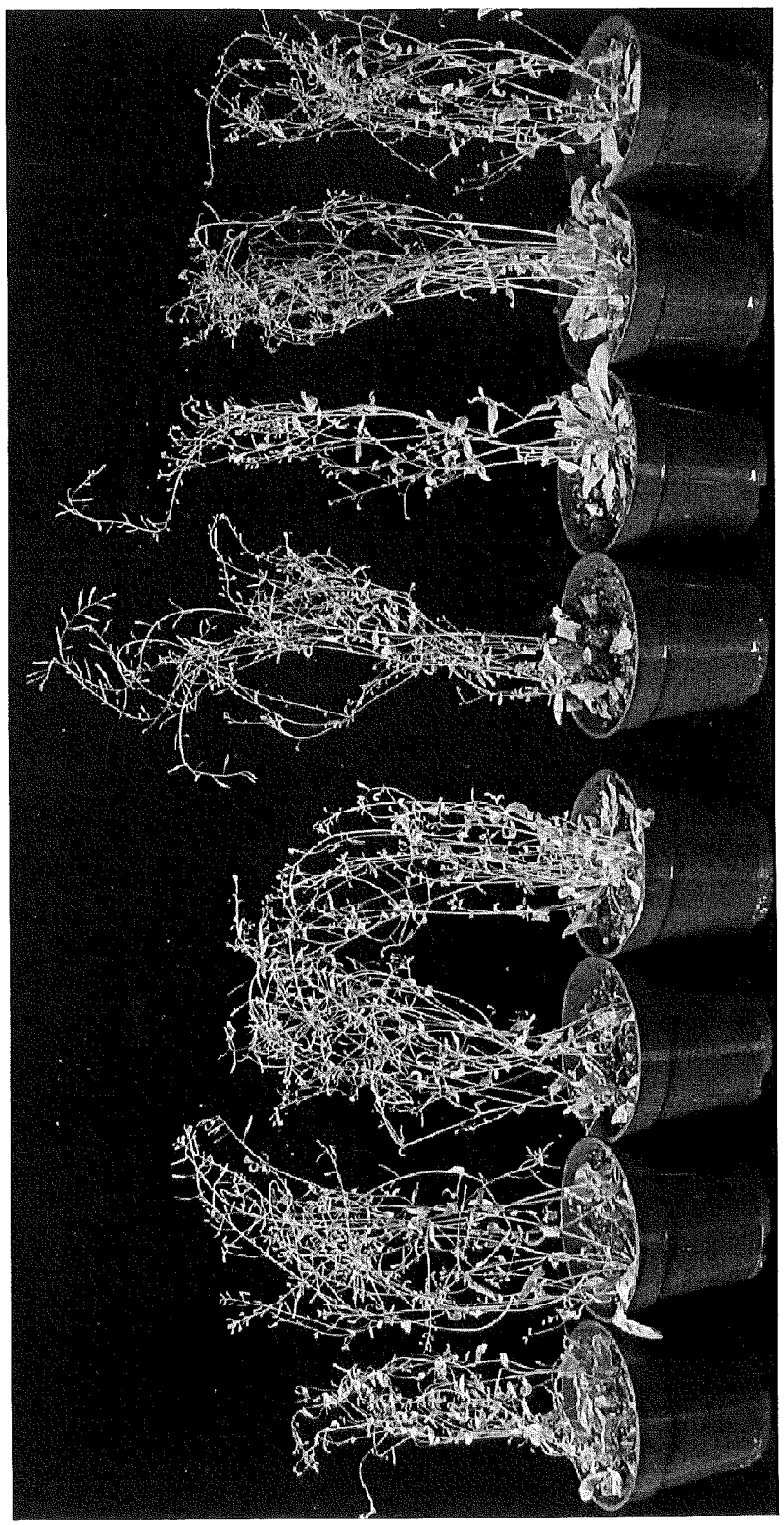
FIG. 3. Transgenic *Arabidopsis* plants (TG) harboring an additional GmCPI1 genomic DNA including promoter, GmCPI1 coding sequence and terminator (pHKHL01) in comparison to wild type (WT) *Arabidopsis* control plants (lacking an additional GmCPI1 genomic DNA including promoter, GmCPI1 coding sequence and terminator (pH- KHL01)) exposed to aphids, thrips and flies. Plants were grown under 8/16 hours (night/day) at 21°-23° C. without any pesticide treatment. Plants were exposed to insects for about 6-7 weeks.

FIG. 3. Transgenic plants (TG) harboring an additional GmCPI1-containing genomic DNA fragment including promoter, GmCPI1 ORF and terminator (pHKHL01) in comparison to wild-type (WT) control plants (i.e., not transformed with pHKHL01) exposed to aphids, thrips and white flies. The plants were grown under 8/16 hours (night/day) at 21°-23° C. without any pesticide treatment.

Figure 4:
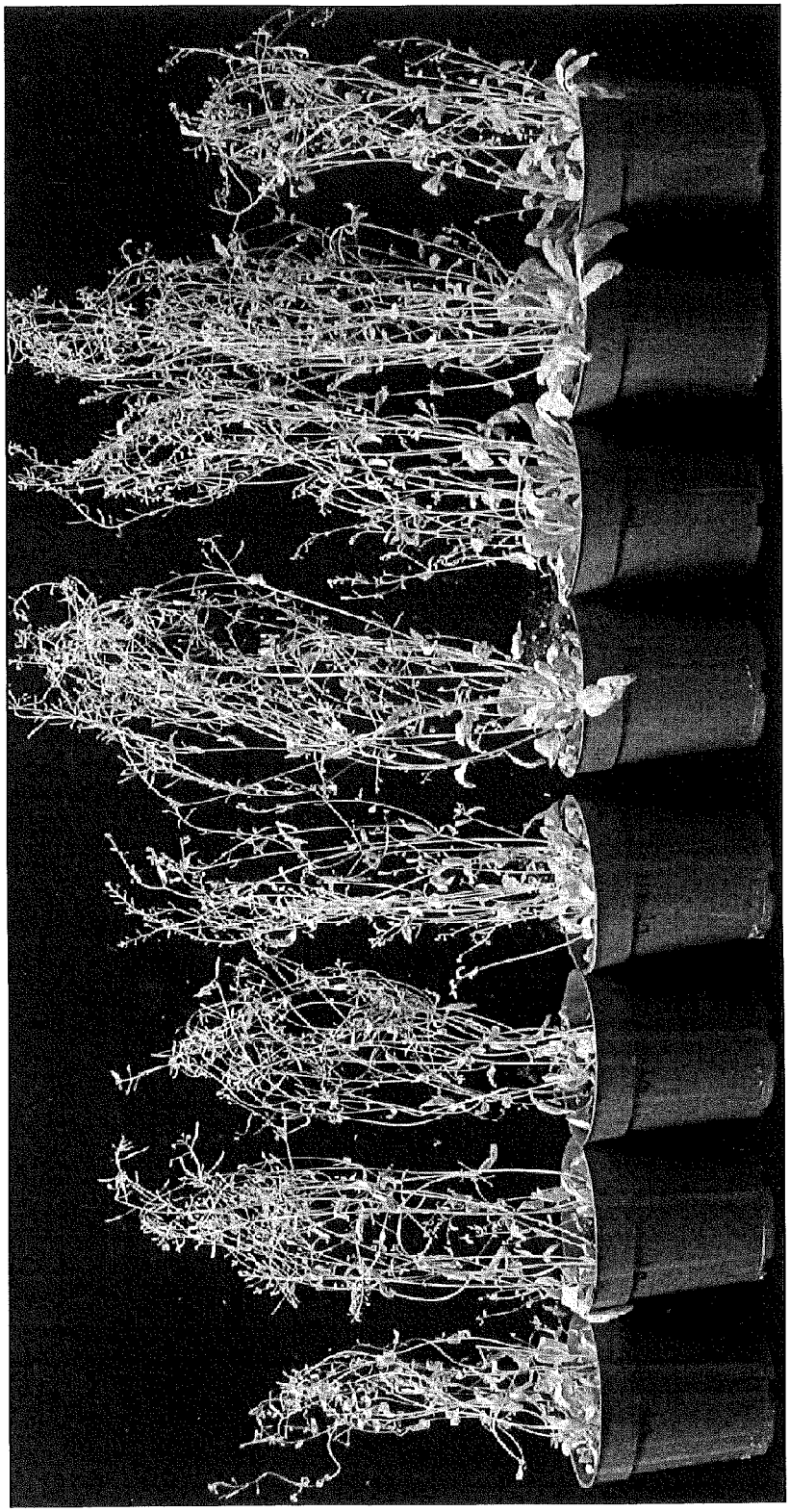
FIG. 4. Transgenic *Arabidopsis* plants (TG2) overexpressing GmCPI1 cDNA of PI437654 under the control of a corn ubiquitin promoter (pHKHL02) in comparison to wild type (WT) control *Arabidopsis* plants (lacking the pHKHL02 construct) exposed to aphids, thrips and flies. The plants were grown under 8/16 hours (night/day) at 21°-23° C. without any pesticide treatment. Shown are images of plants exposed to the insects for about 6-7 weeks.

FIG. 4. Transgenic plants (TG2) harboring the GmCPI1 cDNA (pHKHL02), driven by the corn ubiquitin promoter in comparison to wild-type (WT) control plants (i.e., not transformed with pHKHL02) exposed to aphids, thrips and white flies. The plants were grown under 8/16 hours (night/day) at 21°-23° C. without any pesticide treatment.

Figure 5:
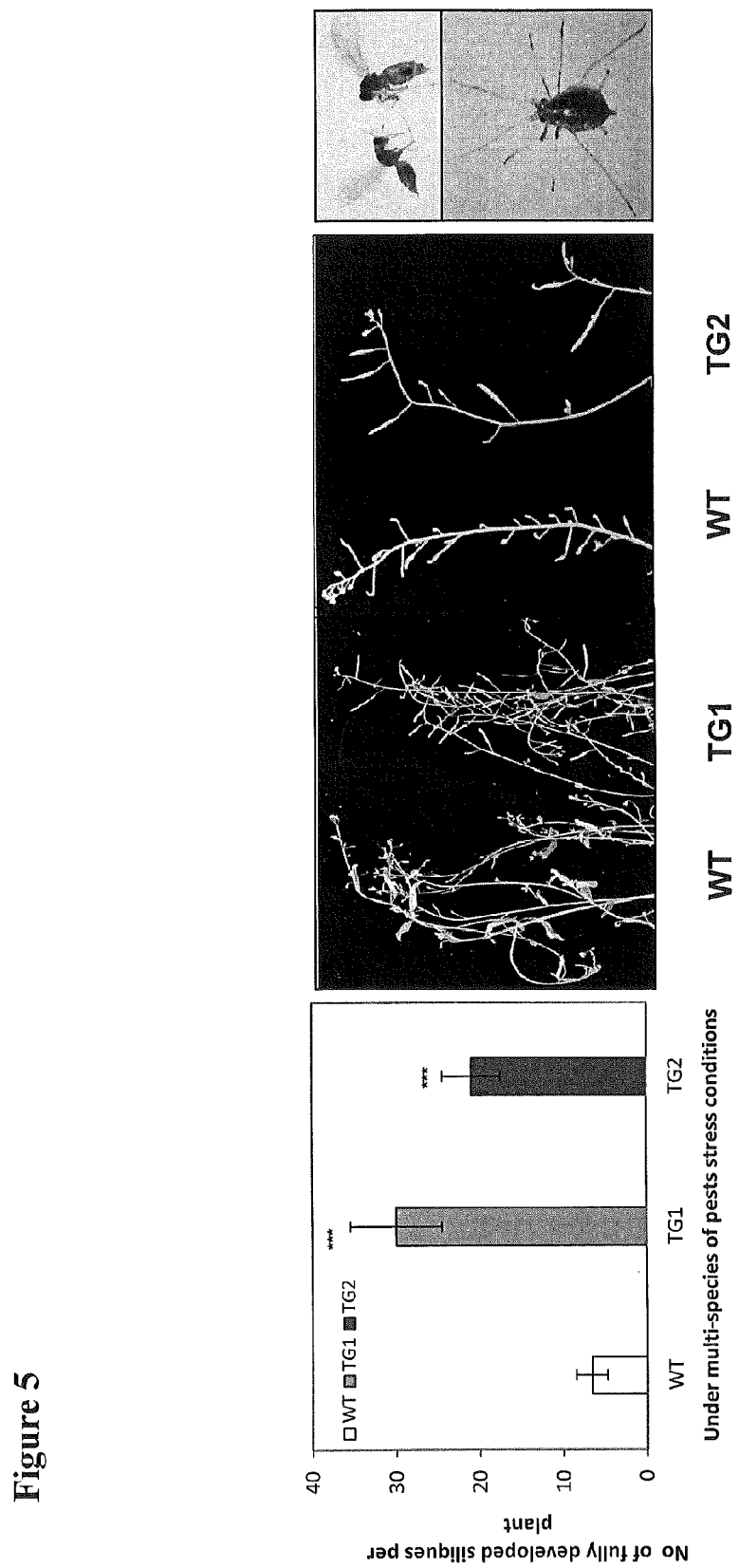
FIG. 5. Transgenic *Arabidopsis* plants overexpressing GmCPI1 (TG1=pHKHL01; TG2=pHKHL02) exhibited significantly higher seed setting rate with normally developed siliques than wild type (WT) control *Arabidopsis* plants (lacking pHKHL01 or pHKHL02). The T2 seeds of TG and seeds of WT were sown in soil and acclimated at 4° C. for 3 days. The stratified seeds were then germinated at 23° C. The germinated plants were grown at the same temperature and under 8/16 hours (night/day) conditions without any pesticide treatment. Three main pests, aphids, thrips and white flies were observed in the plants grown in the growth room. Data are presented as means±SE (N=8) and error bars represent SE. Shown are images of plants exposed to the insects for about 6-7 weeks.

FIG. 5. Transgenic plants (TG1 and TG2) overexpressing GmCPI1 of PI437654 exhibited significantly higher seed setting rate with normally developed siliques than wild type (WT) control plants. The T2 seeds of TG plants and seeds of WT plants were sown in soil and acclimated at 4° C. for 3 days. The stratified seeds were then germinated at 23° C. The germinated plants were grown at the same temperature and under 8/16 hours (night/day) conditions without any pesticide treatment. Three main pests, aphids, thrips and white flies were observed in the plants grown in the growth room. Data are presented as means±SE (n=8) and error bars represent SE.

Figure 6:
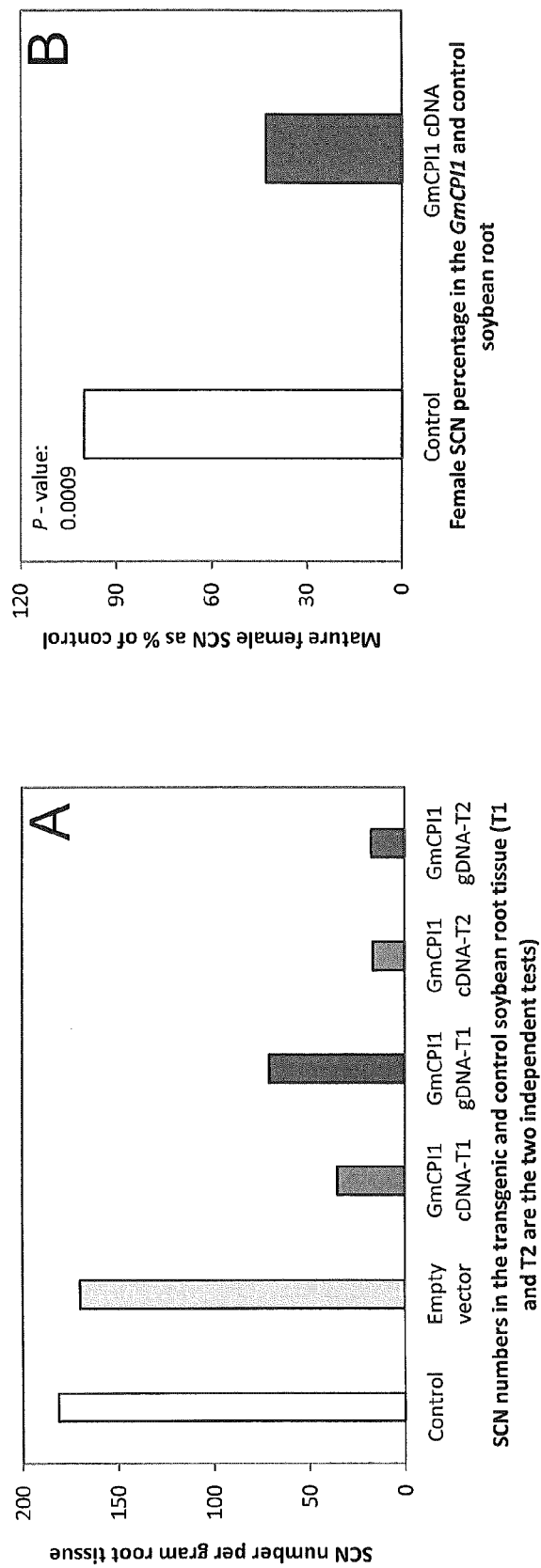
FIGS. 6A-B. Overexpression of GmCPI1 of PI437654 in root tissues of the SCN-susceptible soybean cultivar, Williams 82, inhibited female SCN development. The number of female SCN in transgenic root tissues is lower than that in the non-transformed control plant roots. The assays were conducted by two independent research groups using the same gene constructs. Control=Williams 82 soybean plant with no GmCPI1 transgene of PI437654; Empty vector=Williams 82 soybean plant containing vector that lacks nucleic acid sequence of GmCPI1 of PI437654; GmCPI1 cDNA-T1: Williams 82 soybean plant carrying pHKHL02 construct; GmCPI1 gDNA-T1: Williams 82 soybean plant carrying pHKHL01 construct; GmCPI1-cDNA-T2: Williams 82 soybean plant carrying pHKHL02 construct; GmCPI1 gDNA-T2: Williams 82 soybean plant carrying pHKH101 construct.

FIG. 6. Overexpression of GmCPI1 of PI437654 in roots of the soybean cyst nematode (SCN)-susceptible cultivar Williams 82 led to improved resistance to nematode. A. Williams 82 seeds were used in *Agrobacterium*-mediated root transformation tests. The roots regenerated from callus balls were transformed by using empty vector (only with bar gene cassette), GmCPI1 cDNA vector (pKHKL02) and genomic DNA vector (pHKHL01), respectively. The plants with the transformed root tissues were rinsed and then transplanted into the sand-filled cone-tainers. After 7 days of growth in a moisture room, plant roots were inoculated with 2000 SCN eggs and developed in the greenhouse for 4 weeks. The developed roots were gently rinsed, and the numbers of SCN were counted from the control and the transformed plant roots in two independent tests at Clemson University, B. The female SCN numbers in the transgenic root tissues are significant lower than in the control plant roots. The assay was conducted in a USDA lab, and 45 events were counted.

In summary, these data show that GmCPI1 of PI437654 significantly enhanced soybean SCN resistance when overexpressed in transgenic plants. GmCPI1 of PI437654 also functions in other plant species for enhancing pest resistance. GmCPI1 of PI437654 can be used to genetically engineer various crop species for enhancing pest and disease resistance, producing new breeding materials and new cultivars for commercialization.

Example 2

Figure 9:
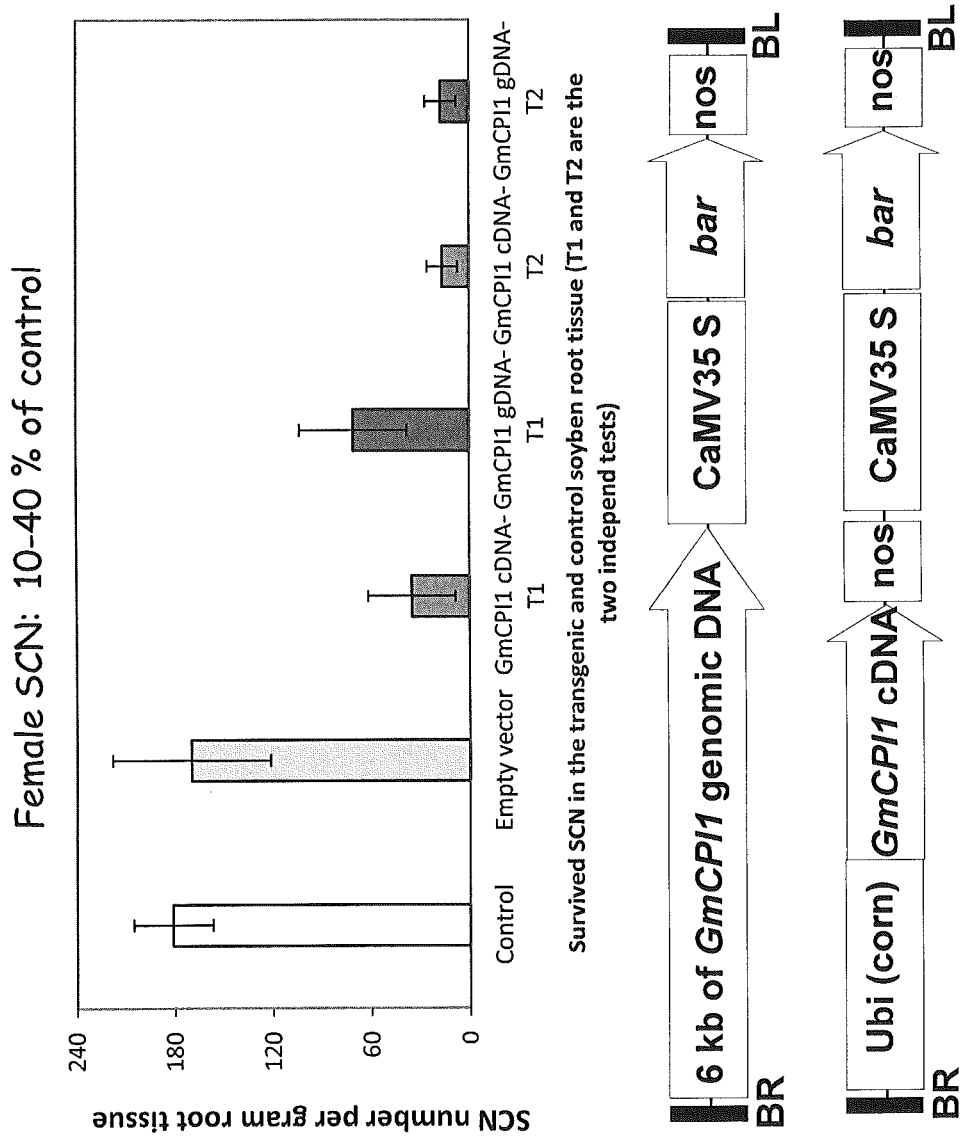
FIG. 9. Overexpression of GmCPI1 of PI437654 in soybean roots leads to enhanced resistance to SCN.

Genetic Engineering of Crop Species with a Soybean Cysteine Protease Inhibitor GmCPI1 for Enhanced Biotic and Abiotic Resistance FIG. 9. Overexpression of GmCPI1 of PI437654 in root tissues of the SCN-susceptible soybean cultivar, Williams 82, inhibited female SCN development. The number of female SCN in transgenic root tissues (transformed with either pHKHL01 or pHKHL02) is significantly lower than that in the non-transformed control soybean plant roots. The assays were conducted by two independent research groups using the same gene constructs.

Figure 10:
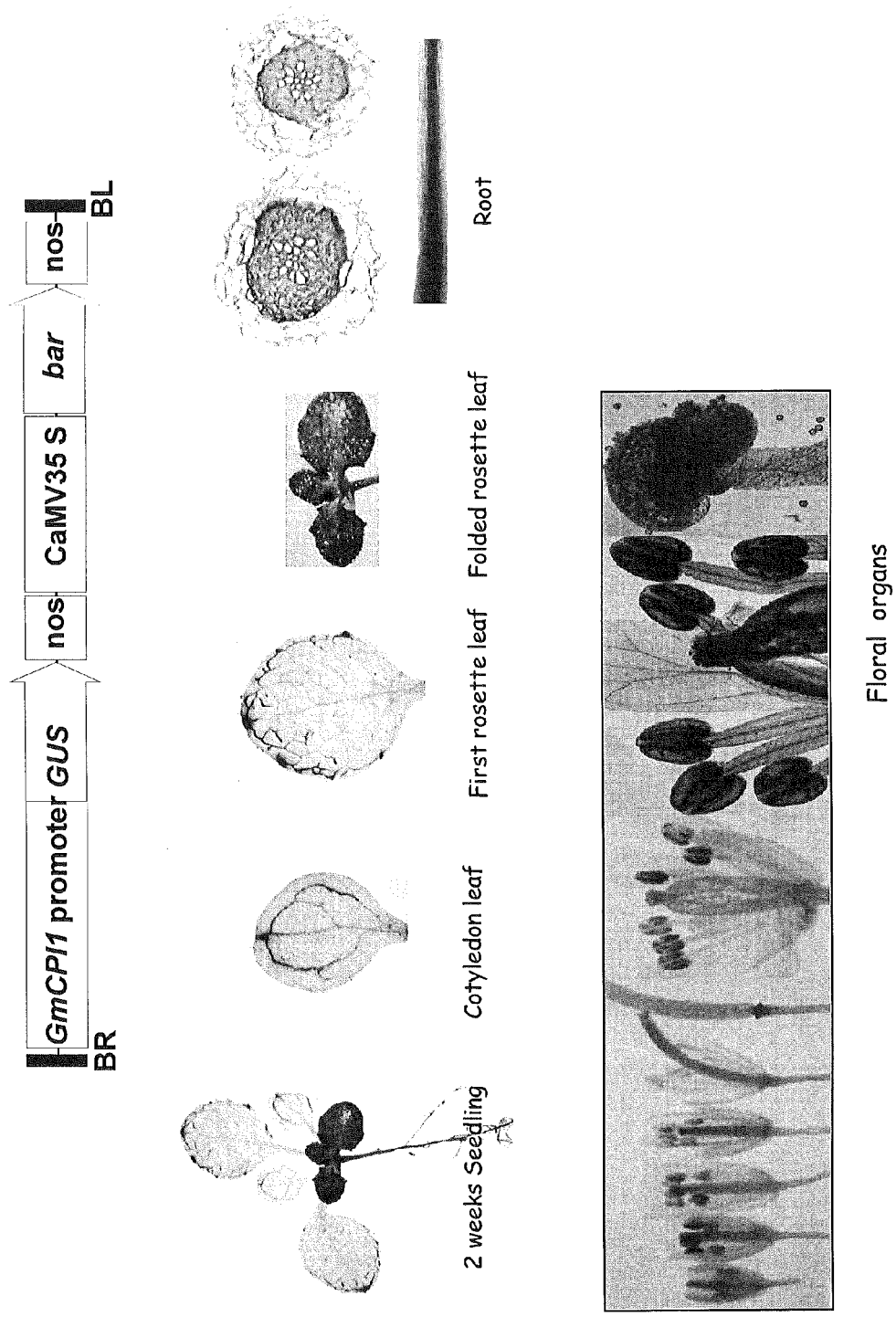
FIG. 10. The activity of GmCPI1 promoter directing GUS expression in transgenic *Arabidopsis* plants.

FIG. 10. This is the GmCPI1 promoter driving β-glucuronidase (GUS) gene transferred into *Arabidopsis thaliana* to study the activity of GmCPI promoter. The results showed that the GUS stain was mainly detected in the root, young leaf, pollen, stigma and immature seeds.

Figure 11:
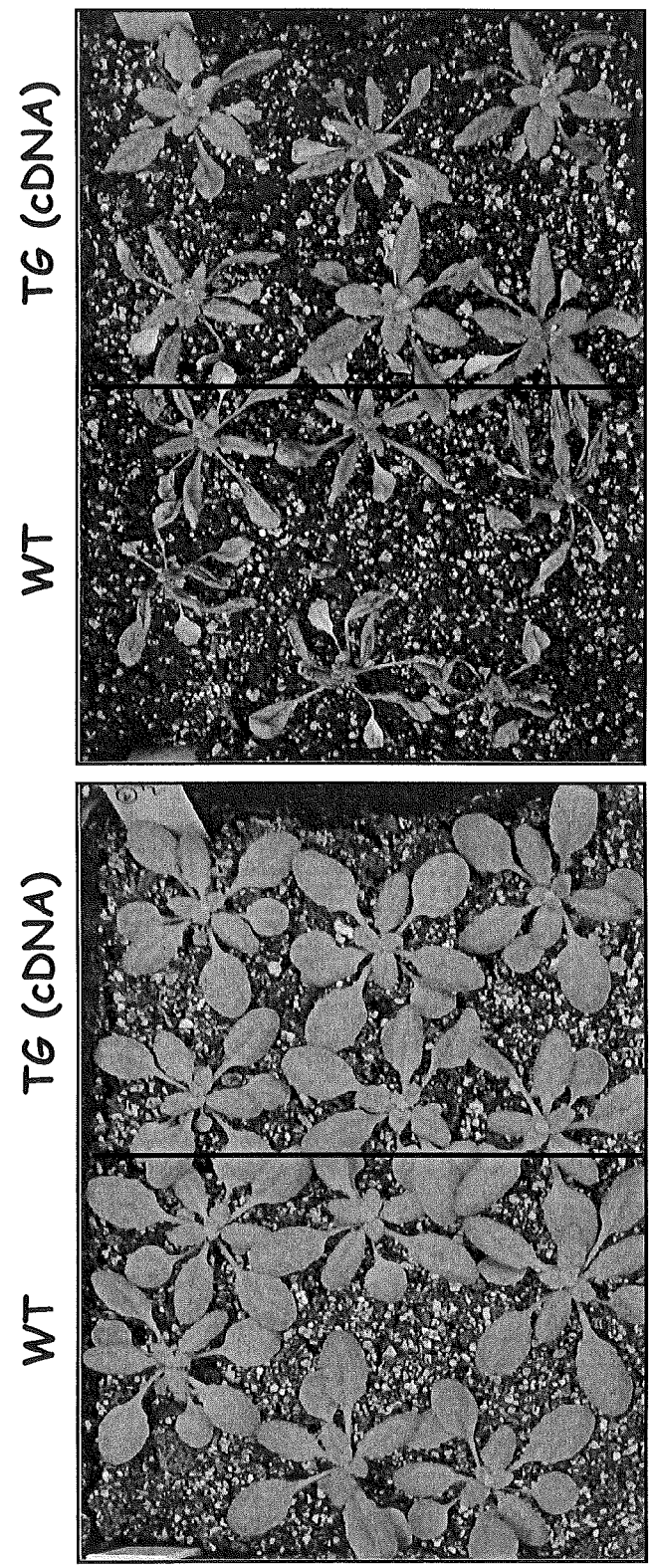
FIG. 11. Overexpression of GmCPI1 of PI437654 enhances plant drought tolerance in transgenic *Arabidopsis*.

FIG. 11. Overexpression of GmCPI1 of PI437654 in transgenic (TG) *Arabidopsis thaliana* changes the adaptation of plants to adverse environmental conditions. The drought stress tests were conducted in a tray (20×15×5 cm$^3$) containing the 3B soil topped with Germination Soil Mix. WT and TG seeds were sown in the same tray with a saturated water soak (then, no more watering until plant recovery). The seeds were cold acclimatized for 3 days at 4° C. The tray was then moved to a growth room under 20° C./24° C. (night/day) for seed germination, and thinning was done 10 days after seed germination. Three tray replicates were used for the experiment. These results show that overexpression of GmCPI1 of PI437654 enhances plant drought tolerance in transgenic *Arabidopsis thaliana*.

Figure 12:
FIG. 12. Overexpression of GmCPI1 of PI437654 enhances plant salt tolerance in transgenic *Arabidopsis*. Five days after treatment.

FIG. 12. Overexpression of GmCPI1 of PI437654 in transgenic (TG) *Arabidopsis* changes the adaptation of plants to adverse environmental conditions. The salt stress tests were conducted in a small tray (20×15×5 cm$^3$) containing the 3B soil topped with Germination Soil Mix. WT and TG seeds were sown in the same tray with a saturated water soak. The seeds were cold acclimatized for 3 days at 4° C., then moved to a growth room under 20° C./24° C. (night/day) for germination. Plant thinning was done 10 days after seed germination. Two liters of 200 mM NaCl were applied for salt stress treatment in a big tray containing 6 small trays. Three tray replicates were used for the experiment performed in the growth room under 20° C./24° C. (night/day). These results show that overexpression of GmCPI1 of PI437654 enhances plant salt tolerance in transgenic *Arabidopsis thaliana*.

Figure 13:
FIG. 13. Overexpression of GmCPI1 of PI437654 enhances plant drought tolerance in transgenic *Arabidopsis*. Seven days after treatment.

FIG. 13. Overexpression of GmCPI1 of PI437654 in transgenic (TG) *Arabidopsis* changes the adaptation of plants to adverse environmental conditions. The salt stress tests were conducted in a small tray (20×15×5 cm$^3$) containing the 3B soil topped with Germination Soil Mix. WT and TG seeds were sown in the same tray with a saturated water soak. The seeds were cold acclimatized for 3 days at 4° C., then moved to a growth room under 20° C./24° C. (night/day) for germination. Plant thinning was done 10 days after seed germination. Two liters of 200 mM NaCl were applied for salt stress treatment in a big tray containing 6 small trays. Three tray replicates were used for the experiment performed in the growth room under 20° C./24° C. (night/day). These results show that overexpression of GmCPI1 of PI437654 enhances plant salt tolerance in transgenic *Arabidopsis thaliana*.

The foregoing is illustrative of the present invention, and is not to be construed as limiting thereof. The invention is defined by the following claims, with equivalents of the claims to be included therein.

All publications, patent applications, patents and other references cited herein are incorporated by reference in their entireties for the teachings relevant to the sentence and/or paragraph in which the reference is presented.

TABLE 1

GmCPI1: One amino acid difference between resistant and susceptible soybean cultivars.

| Cultivar | Encoding sequence | amino acid | Resistance to SCN |
|---|---|---|---|
| PI437654 | GAG | Glutamic acid | R |
| PI548402 | GAG | Glutamic acid | R |
| PI548316 | AAG | Lysine | S |
| PI209332 | GAG | Glutamic acid | R |
| WILLIAMS 82 | AAG | Lysine | S |
| PI548658 | AAG | Lysine | S |
| PI90763 | GAG | Glutamic acid | R |
| PI89772 | GAG | Glutamic acid | R |
| PI88788 | GAG | Glutamic acid | R |
| MOTTE | GAG | Glutamic acid | R |
| MAXCY | GAG | Glutamic acid | R |
| DOLLIN | AAG | Lysine | S |

That which is claimed is:

1. A nucleic acid construct comprising a nucleotide sequence encoding the amino acid sequence of SEQ ID NO:3 and further comprising a selectable marker sequence.

2. A nucleic acid construct, comprising, in the following order from 5' to 3':
   a) a first promoter that is heterologous to GmCPI1;
   b) the nucleotide sequence encoding the amino acid sequence of SEQ ID NO:3 operably associated with the first promoter; and
   c) a first termination sequence.

3. The nucleic acid construct of claim 2, further comprising in the following order from 5' to 3' after the first termination sequence:
   d) a second promoter;
   e) a nucleotide sequence encoding a selectable marker operably associated with the second promoter; and
   f) a second termination sequence.

4. A transformed plant cell comprising the nucleic acid construct of claim 1.

5. A transgenic plant comprising the nucleic acid construct of claim 1.

6. A transgenic seed comprising the nucleic acid construct of claim 1.

7. A method of producing a transgenic plant having enhanced tolerance to biotic and/or abiotic stress, comprising:
   a) transforming a cell of a plant with the nucleic acid construct of claim 1; and
   b) regenerating the transgenic plant from the transformed plant cell, wherein the transgenic plant has enhanced tolerance to biotic and/or abiotic stress as compared with a plant that is not transformed with said nucleic acid construct and wherein the plant is a soybean plant, an *Arabidopsis* plant, a forage grass plant, a turfgrass plant, a tobacco plant, a tomato plant, a potato plant a pea plant a green bean plan ma bean plant, a cauliflower plant, a broccoli plant, a cabbage plant, an oil seed plant, a cotton plant, a beet plant, a sugar beet plant, a spinach plant, a lettuce plant, a cucumber plant, a wheat plant, a rice plant or a peanut plant.

8. The method of claim 7, wherein the stress is biotic stress.

9. The method of claim 8, wherein the biotic stress is insect damage.

10. The method of claim 7, wherein the stress is abiotic stress.

11. The method of claim 10, wherein the abiotic stress is salt stress and/or drought stress.

12. A transgenic plant produced by the method of claim 7.

13. A crop comprising a plurality of transgenic plants of claim 5, planted together in an agricultural field, a golf course, a residential lawn, a road side, an athletic field, and/or a recreational field.

14. A transformed plant cell comprising the nucleic acid construct of claim 2.

15. A transgenic plant comprising the nucleic acid construct of claim 2.

16. A transgenic seed comprising the nucleic acid construct of claim 2.

17. A method of producing a transgenic plant having enhanced tolerance to biotic and/or abiotic stress, comprising:
   a) transforming a cell of a plant with the nucleic acid construct of claim 2; and
   b) regenerating the transgenic plant from the transformed plant cell, wherein the transgenic plant has enhanced tolerance to biotic and/or abiotic stress as compared with a plant that is not transformed with said nucleic acid construct and wherein the plant is a soybean plant, an *Arabidopsis* plant, a forage grass plant, a turfgrass plant, a tobacco plant, a tomato plant, a potato plant, a pea plant, a green bean plant, a lima bean plant, a cauliflower plant, a broccoli plant, a cabbage plant, an oil seed plant, a cotton plant, a beet plant, a sugar beet plant, a spinach plant, a lettuce plant, a cucumber plant, a wheat plant, a rice plant or a peanut plant.

18. The method of claim 17, wherein the stress is biotic stress.

19. The method of claim 18, wherein the biotic stress is insect damage.

20. The method of claim 17, wherein the stress is abiotic stress.

21. The method of claim 20, wherein the abiotic stress is salt stress and/or drought stress.

22. A transgenic plant produced by the method of claim 17.

23. A crop comprising a plurality of transgenic plants of claim 15, planted together in an agricultural field, a golf course, a residential lawn, a road side, an athletic field, and/or a recreational field.

* * * * *

UNITED STATES PATENT AND TRADEMARK OFFICE
CERTIFICATE OF CORRECTION

PATENT NO.        : 9,441,241 B2
APPLICATION NO.   : 14/173639
DATED             : September 13, 2016
INVENTOR(S)       : Luo et al.

It is certified that error appears in the above-identified patent and that said Letters Patent is hereby corrected as shown below:

In the Specification

Column 4, Line 34: Please correct "§2111,03." to read -- § 2111.03. --

In the Claims

Column 53, Claim 7, Line 65: Please correct "plant a green bean plan ma"
to read -- plant, a green bean plant, a lima --

Signed and Sealed this
Thirtieth Day of May, 2017

Michelle K. Lee
*Director of the United States Patent and Trademark Office*